(12) United States Patent
Jakobsen et al.

(10) Patent No.: US 8,217,144 B2
(45) Date of Patent: Jul. 10, 2012

(54) HIGH AFFINITY MELAN-A T CELL RECEPTORS

(75) Inventors: Bent Karsten Jakobsen, Abingdon (GB); Nathaniel Ross Liddy, Abingdon (GB)

(73) Assignee: Immunocore Ltd., Oxon (GB)

( * ) Notice: Subject to any disclaimer, the term of this patent is extended or adjusted under 35 U.S.C. 154(b) by 908 days.

(21) Appl. No.: 11/915,766

(22) PCT Filed: May 31, 2006

(86) PCT No.: PCT/GB2006/001980
§ 371 (c)(1),
(2), (4) Date: Jun. 18, 2008

(87) PCT Pub. No.: WO2006/129085
PCT Pub. Date: Dec. 7, 2006

(65) Prior Publication Data
US 2008/0292549 A1    Nov. 27, 2008

(30) Foreign Application Priority Data

Jun. 1, 2005  (GB) .................................. 0511124.0

(51) Int. Cl.
  C07K 1/00      (2006.01)
  C07K 14/00     (2006.01)
  C07K 17/00     (2006.01)
(52) U.S. Cl. ...................................................... 530/350
(58) Field of Classification Search ........................ None
  See application file for complete search history.

(56) References Cited

FOREIGN PATENT DOCUMENTS

| WO | WO 2004/044004 A2 |   | 5/2004 |
|----|-------------------|---|--------|
| WO | WO 2004050705 A2  | * | 6/2004 |
| WO | WO 2005/113595 A2 |   | 12/2005 |
| WO | WO 2005/114215 A2 |   | 12/2005 |

OTHER PUBLICATIONS

Dutoit et al., 2002, Canc. Immunity. vol. 2: 1-13.*
Manning et al., 1999, J. Exp. Med. vol. 189: 461-470.*
Lefranc et al., "IMGT unique numbering for immunoglobulin and T cell receptor constant domains and Ig superfamily C-like domains" Developmental and Comparative Immunology Pergamon Press, US, vol. 29, No. 3, 2005, pp. 185-203, XP004657549.
Li et al., "Directed evolution of human T-cell receptors with picomolar affinities by phage display" Nature Biotechnology, vol. 23, No. 3, Mar. 2005, pp. 349-354, XP002336795.
Valmori et al., "Diversity of the fine specificity displayed by HLA-A0201-Restricted CTL specific for the immunodominant Melan-A/MART-1 Antigenic peptide" The Journal of Immunology, vol. 161, 1998, pp. 6956-6962, XP002408723.

* cited by examiner

*Primary Examiner* — Amy Juedes
(74) *Attorney, Agent, or Firm* — Vedder Price P.C.; Thomas J. Kowalski; Smitha B. Uthaman

(57) ABSTRACT

The present invention provides TCRs having an affinity ($K_D$) of less than or equal to 3 μM, and/or an off-rate ($k_{off}$) of $1 \times 10^{-3}$ $S^{-1}$ or slower, for the AAGIGILTV-HLA-A*0201 complex. Such TCRs are useful, either alone or associated with a therapeutic agent, for targeting cancer cells presenting that complex.

49 Claims, 33 Drawing Sheets

Figure 1a

Figure 8A:
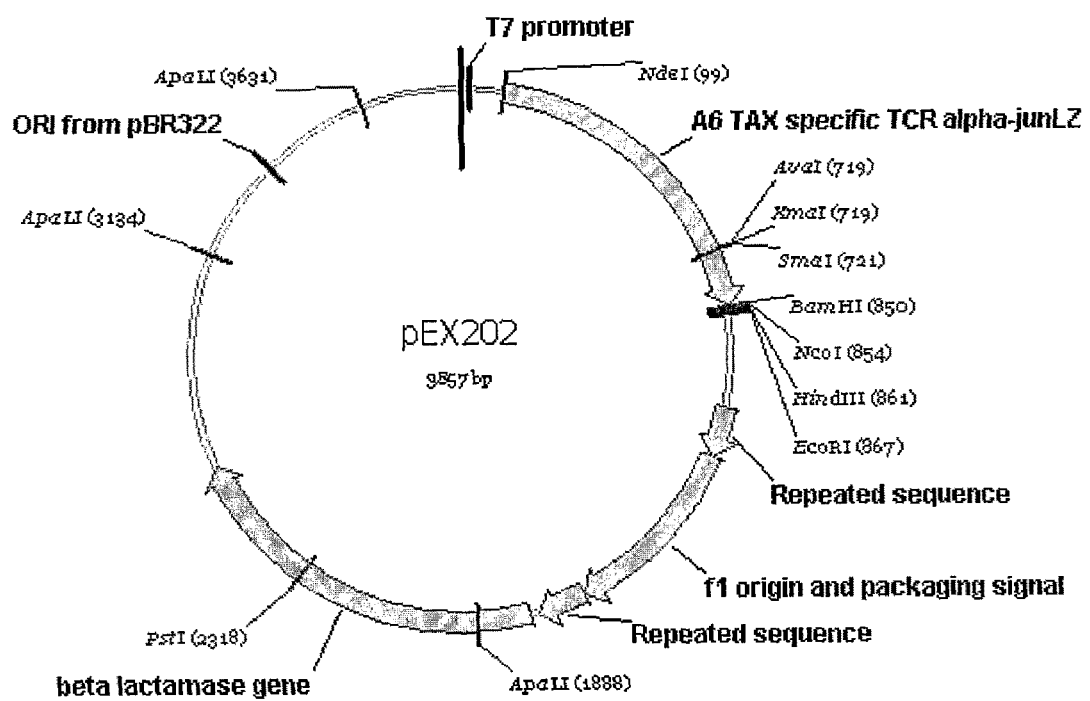

```
              10                    20
              *                     *
M Q K E V E Q N S G P L S V P E G A I A S L N C T Y S D R 30                  40                    50
*                   *                     *
G S Q S F F W Y R Q Y S G K S P E L I M F I Y S N G D K E 60                  70                    80
*                   *                     *
D G R F T A Q L N K A S Q Y V S L L I R D S Q P S D S A T 90                    100                   110
    *                     *                     *
Y L C A V N V A G K S T F G D G T T L T V K P
```

(SEQ ID No: 1)

Figure 1b

```
          10                    20
           *                     *
M S Q T I H Q W P A T L V Q P V G S P L S L E C T V E G T 30                    40                    50
 *                     *                     *
S N P N L Y W Y R Q A A G R G L Q L L F Y S V G I G Q I S 60                    70                    80
      *                     *                     *
S E V P Q N L S A S R P Q D R Q F I L S S K K L L L S D S 90                   100                   110
      *                     *                     *
G F Y L C A W S E T G L G T G E L F F G E G S R L T V L
```

(SEQ ID No: 2)

Figure 2a atgcaaaaagaagttgaacaaaattctggaccccctcagtgttccagagggagccattgcctctctcaactgcacttacagtga
ccgaggttcccagtccttcttctggtacagacaatattctgggaaaagccctgagttgataatgttcatatactccaatggtgac
aaagaagatggaaggtttacagcacagctcaataaagccagccagtatgtttctctgctcatcagagactcccagcccagtg
attcagccacctacctctgtgccgtgaacgttgcaggcaaatcaacctttggggatgggactacgctcactgtgaagccaaat
atccagaaccctgaccctgccgtgtaccagctgagagactctaagtcgagtgacaagtctgtctgcctattcaccgattttgat
tctcaaacaaatgtgtcacaaagtaaggattctgatgtgtatatcacagacaaaactgtgctagacatgaggtctatggacttc
aagagcaacagtgctgtggcctggagcaacaaatctgactttgcatgtgcaaacgccttcaacaacagcattattccagaag
acaccttcttccccagcccagaaagttcctaagcttga
(SEQ ID No: 3)

Figure 2b atgtctcagactattcatcaatggccagcgaccctggtgcagcctgtgggcagcccgctctctctggagtgcactgtggagg
gaacatcaaaccccaacctatactggtaccgacaggctgcaggcaggggcctccagctgctcttctactccgttggtattgg
ccagatcagctctgaggtgccccagaatctctcagcctccagaccccaggaccggcagttcatcctgagttctaagaagctc
ctcctcagtgactctggcttctatctctgtgcctggtccgagacagggttaggcaccggggagctgttttttggagaaggctct
aggctgaccgtactggaggacctgaaaaacgtgttcccacccgaggtcgctgtgtttgagccatcagaagcagagatctcc
cacacccaaaaggccacactggtgtgcctggccaccggtttctaccccgaccacgtggagctgagctggtgggtgaatgg
gaaggaggtgcacagtggggtcagcacagacccgcagcccctcaaggagcagcccgccctcaatgactccagatacgc
tctgagcagccgcctgagggtctcggccaccttctggcaggaccccgcaaccacttccgctgtcaagtccagttctacgg
gctctcggagaatgacgagtggacccaggatagggccaaacccgtcacccagatcgtcagcgccgaggcctggggtag
agcagactaagcttga
(SEQ ID No: 4)

Figure 3a

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P N I Q N P D
P A V Y Q L R D S K S S D K S V C L F T D F D S Q T N V S
Q S K D S D V Y I T D K T V L D M R S M D F K S N S A V A
W S N K S D F A C A N A F N N S I I P E D T F F P S P E S
S
```
(SEQ ID No: 5)

Figure 3b

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V S T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID No: 6)

Figure 4a tata<u>catatg</u>caaaaagaagttgaacaaaattctggaccctcagtgttccagagggagccattgcctctctcaactgcactta
cagtgaccgaggttcccagtccttcttctggtacagacaatattctgggaaaagccctgagttgataatgttcatatactccaat
ggtgacaaagaagatggaaggtttacagcacagctcaataaagccagccagtatgtttctctgctcatcagagactcccagc
ccagtgattcagccacctacctctgtgccgtgaacgttgcaggcaaatcaacctttggggatgggactacgctcactgtgaa
gccaaatatccagaaccctgaccctgccgtgtaccagctgagagactctaagtcgagtgacaagtctgtctgcctattcacc
gattttgattctcaaacaaatgtgtcacaaagtaaggattctgatgtgtatatcacagacaaa<u>tgt</u>gtgctagacatgaggtctat
ggacttcaagagcaacagtgctgtggcctggagcaacaaatctgactttgcatgtgcaaacgccttcaacaacagcattattc
cagaagacaccttcttccccagcccagaaagttcc<u>taagctt</u>ga
(SEQ ID No: 7)

Figure 4b tata<u>catatg</u>tctcagactattcatcaatggccagcgaccctggtgcagcctgtgggcagcccgctctctctggagtgcactgt
ggagggaacatcaaaccccaacctatactggtaccgacaggctgcaggcaggggcctccagctgctcttctactccgttgg
tattggccagatcagctctgaggtgccccagaatctctcagcctccagaccccaggaccggcagttcatcctgagttctaag
aagctcctcctcagtgactctggcttctatctctgtgcctggtccgagacagggttaggcaccggggagctgttttttggagaa
ggctctaggctgaccgtactggaggacctgaaaaacgtgttcccacccgaggtcgctgtgtttgagccatcagaagcagag
atctcccacacccaaaaggccacactggtgtgcctggccaccggtttctaccccgaccacgtggagctgagctggtgggtg
aatgggaaggaggtgcacagtggggtctg<u>g</u>acagaccgcagcccctcaaggagcagcccgccctcaatgactccagat
acgctctgagcagccgcctgagggtctcggccaccttctggcaggaccccgcaaccacttccgctgtcaagtccagttct
acgggctctcggagaatgacgagtggacccaggataggccaaacccgtcacccagatcgtcagcgccgaggcctggg
gtagagcagact<u>aagctt</u>ga
(SEQ ID No: 8)

Figure 5a

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P N I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S
```
(SEQ ID No: 9)

Figure 5b

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID No: 10)

Figure 6

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N D̲ G̲ G R L̲ T F G D G T T L T V K P
(SEQ ID No: 11)

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N V G̲ G R̲ L̲ T F G D G T T L T V K P
(SEQ ID No: 12)

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N D̲ A G R̲ L̲ T F G D G T T L T V K P
(SEQ ID No: 13)

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N D̲ G̲ G K L̲ T F G D G T T L T V K P
(SEQ ID No: 14)

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N D̲ G̲ G R̲ S T F G D G T T L T V K P
(SEQ ID No: 15)

Figure 6 (Cont.)

```
M Q K E V E Q N S G P L S V P E G A I A S L N C T Y S D R
G S Q S F F W Y R Q Y S G K S P E L I I F I Y S N G D K E
D G R F T A Q L N K A S Q Y V S L L I R D S Q P S D S A T
Y L C A V N V G G Y L L F G D G T T L T V K P
```
(SEQ ID No: 16)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N P G G V L T F G D G T T L T V K P
```
(SEQ ID No: 17)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N P G G L L T F G D G T T L T V K P
```
(SEQ ID No: 18)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N S G N H M T F G D G T T L T V K P
```
(SEQ ID No: 19)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N L S P G L T F G D G T T L T V K P
```
(SEQ ID No: 20)

Figure 6 (Cont.)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N V G V I L R F G D G T T L T V K P
```
(SEQ ID No: 21)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N N G M P S T F G D G T T L T V K P
```
(SEQ ID No: 22)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N V G L I L L F G D G T T L T V K P
```
(SEQ ID No: 23)

```
M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N S E R P R T F G D G T T L T V K P
```
(SEQ ID No: 24)

Figure 7a

N I Q N P D P A V Y Q L R D S K S S D K S V C L F T
D F D S Q T N V S Q S K D S D V Y I T D K
(SEQ ID No: 25)

Figure 7b

E D L N K V F P P E V A V F E P S E A E I S H T Q K A T
L V C L A T G F F P D H V E L S W W V N G K E V H S G V
(SEQ ID No: 26)

Figure 7c

E D L K N V F P P E V A V F E P S E A E I S H T Q K A T
L V C L A T G F Y P D H V E L S W W V N G K E V H S G V
(SEQ ID No: 27)

Figure 8b gatctcgatcccgcgaaattaatacgactcactatagggagaccacaacggtttccctctagaaataattttgtttaactttaaga
aggagatatacatatgcagaaggaagtggagcagaactctggaccccctcagtgttccagagggagccattgcctctctcaa
ctgcacttacagtgaccgaggttccccagtccttcttctggtacagacaatattctgggaaaagccctgagttgataatgtccata
tactccaatggtgacaaagaagatggaaggtttacagcacagctcaataaagccagccagtatgtttctctgctcatcagaga
ctcccagcccagtgattcagccacctacctctgtgccgttacaactgacagctgggggaaattgcagtttggagcagggacc
caggttgtggtcaccccagatatccagaaccctgaccctgccgtgtaccagctgagagactctaaatccagtgacaagtctg
tctgcctattcaccgatttttgattctcaaacaaatgtgtcacaaagtaaggattctgatgtgtatatcacagacaaaactgtgcta
gacatgaggtctatggacttcaagagcaacagtgctgtggcctggagcaacaaatctgactttgcatgtgcaaacgccttca
acaacagcattattccagaagacaccttcttccccagcccagaaagttcccccgggggtagaatcgcccggctggaggaa
aaagtgaaaaccttgaaagctcagaactcggagctggcgtccacggccaacatgctcagggaacaggtggcacagcttaa
acagaaagtcatgaactactaggatccatggtaagcttgaattccgatccggctgctaacaaagcccgaaaggaagctgag
ttggctgctgccaccgctgagcaataactagcataaccccttggggcctctaaacgggtcttgaggggttttttgctgaaagg
aggaactatatccggataattcttgaagacgaaagggcctcgtgatacgcctatttttataggttaatgtcatgataataatggtt
tcttagacgtcaggtggcacttttcggggaaatgtgcgcggaaccccctatttgtttatttttctaaatacattcaaatatgtatccg
ctcatgagacaataaccctgataaatgcttcaataatattttgttaaaattcgcgttaaattttgttaaatcagctcattttttaacca
ataggccgaaatcggcaaaatcccttataaatcaaaagaatagaccgagatagggttgagtgttgttccagtttggaacaaga
gtccactattaaagaacgtggactccaacgtcaaaggcgaaaaaccgtctatcagggcgatggcccactacgtgaaccat
caccctaatcaagttttttggggtcgaggtgccgtaaagcactaaatcggaaccctaaagggagcccccgatttagagcttg
acggggaaagccggcgaacgtggcgagaaaggaagggaagaaagcgaaaggagcgggcgctagggcgctggcaag
tgtagcggtcacgctgcgcgtaaccaccacacccgccgcgcttaatgcgccgctacagggcgcgtcaggtggcactttcg
gggaaatgtgcgcggaaccccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcattttgccttcct
gttttttgctcacccagaaacgctggtgaaagtaaaagatgctgaagatcagttgggtgcacgagtgggttacatcgaactgg
atctcaacagcggtaagatccttgagagttttcgccccgaagaacgttttccaatgatgagcacttttaaagttctgctatgtgg
cgcggtattatcccgtgttgacgccgggcaagagcaactcggtcgccgcatacactattctcagaatgacttggttgagtact
caccagtcacagaaaagcatcttacggatggcatgacagtaagagaattatgcagtgctgccataaccatgagtgataacac
tgcggccaacttacttctgacaacgatcggaggaccgaaggagctaaccgcttttttgcacaacatgggggatcatgtaact
cgccttgatcgttgggaaccggagctgaatgaagccataccaaacgacgagcgtgacaccacgatgcctgcagcaatggc
aacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtct
cgcggtatcattgcagcactggggccagatggtaagccctcccgtatcgtagttatctacacgacggggagtcaggcaact
atggatgaacgaaatagacagatcgctgagataggtgcctcactgattaagcattggtaactgtcagaccaagtttactcatat
atactttagattgatttaaaacttcattttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctg
ctgcttgcaaacaaaaaaaccaccgctaccagcggtggtttgtttgccggatcaagagctaccaactctttttccgaaggtaa
ctggcttcagcagagcgcagataccaaatactgtccttctagtgtagccgtagttaggccaccacttcaagaactctgtagca
ccgcctacatacctcgctctgctaatcctgttaccagtggctgctgccagtggcgataagtcgtgtcttaccgggttggactca
agacgatagttaccggataaggcgcagcggtcgggctgaacggggggttcgtgcacacagcccagcttggagcgaacg
acctacaccgaactgagatacctacagcgtgagctatgagaaagcgccacgcttcccgaagggagaaaggcggacaggt
atccggtaagcggcagggtcggaacaggagagcgcacgagggagcttccaggggggaaacgcctggtatctttatagtcct

Figure 8b (Cont.)

gtcgggtttcgccacctctgacttgagcgtcgattttgtgatgctcgtcaggggggcggagcctatggaaaaacgccagca
acgcggccttttacggttcctggccttttgctggccttttgctcacatgttctttcctgcgttatccctgattctgtggataaccgt
attaccgcctttgagtgagctgataccgctcgccgcagccgaacgaccgagcgcagcgagtcagtgagcgaggaagcgg
aagagcgcctgatgcggtattttctccttacgcatctgtgcggtatttcacaccgcaatggtgcactctcagtacaatctgctct
gatgccgcatagttaagccagtatacactccgctatcgctacgtgactgggtcatggctgcgccccgacacccgccaacac
ccgctgacgcgccctgacgggcttgtctgctcccggcatccgcttacagacaagctgtgaccgtctccgggagctgcatgt
gtcagaggttttcaccgtcatcaccgaaacgcgcgaggcag
(SEQ ID NO: 28)

Figure 9a

M Q K E V E Q N S G P L S V P E G A I A S L N C T Y S D R
G S Q S F F W Y R Q Y S G K S P E L I M F I Y S N G D K E
D G R F T A Q L N K A S Q Y V S L L I R D S Q P S D S A T
Y L C A V N D G G R L T F G D G T T L T V K P N I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S (SEQ ID NO: 29)

Figure 9b

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D P G A P T S S T K K T Q L Q L
E H L L L D L Q M I L N G I N N Y K N P K L T R M L T F K
F Y M P K K A T E L K H L Q C L E E E L K P L E E V L N L
A Q S K N F H L R P R D L I S N I N V I V L E L K G S E T
T F M C E Y A D E T A T I V E F L N R W I T F C Q S I I S
T L T (SEQ ID NO: 30)

WT MEL MTCR BINDING TO WT HLA-A2 9mer

Figure 11a ctcgagccgccaccatgatgaagagcctgcgggtgctgctggtgatcctgtggctgcagctgagctgggtgtggagccag
cagaaggaggtggagcagaacagcggcccccctgagcgtgcccgagggcgccatcgccagcctgaactgcacctacag
cgaccggggcagccagagcttcttctggtatcggcagtacagcggcaagagccccgagctgattatgttcatctacagcaa
cggcgacaaggaggacggccggttcaccgcccagctgaacaaggccagccagtatgtgagcctgctgatccgggacag
ccagcccagcgacagcgccacctacctgtgcgccgtgaacgtggctgggaagagccacttcggcgacggcaccaccct
gaccgtgaagcccaacatccagaaccccgaccccgccgtgtaccagctgcgggacagcaagagcagcgacaagtctgt
gtgcctgttcaccgacttcgacagccagaccaatgtgagccagagcaaggacagcgacgtgtacatcaccgacaagacc
gtgctggacatgcggagcatggacttcaagagcaacagcgccgtggcctggagcaacaagagcgacttcgcctgcgcca
acgccttcaacaacagcatcatccccgaggacaccttttcccccagccccgagagcagctgcgacgtgaaactggtggag
aagagcttcgagaccgacaccaacctgaacttccagaacctgagcgtgatcggcttcagaatcctgctgctgaaagtggct
gggttcaacctgctgatgaccctgcggctgtggagcagctaaacgcgt
(SEQ ID NO: 31)

Figure 11b

MEL wt alpha protein sequence
MMKSLRVLLVILWLQLSWVWSQQKEVEQNSGPLSVPEGAIASLNCTYSDRGSQSFFWY
RQYSGKSPELIMFIYSNGDKEDGRFTAQLNKASQYVSLLIRDSQPSDSATYLCAVNVA
GKSTFGDGTTLTVKPNIQNPDPAVYQLRDSKSSDKSVCLFTDFDSQTNVSQSKDSDVY
ITDKTVLDMRSMDFKSNSAVAWSNKSDFACANAFNNSIIPEDTFFPSPESSCDVKLVE
KSFETDTNLNFQNLSVIGFRILLLKVAGFNLLMTLRLWSS
(SEQ ID NO: 32)

Figure 12a ctcgagccgccaccatgatgaagagcctgcgggtgctgctggtgatcctgtggctgcagctgagctgggtgtggagccag
cagaaggaggtggagcagaacagcggccccctgagcgtgcccgagggcgccatcgccagcctgaactgcacctacag
cgaccgggggcagccagagcttcttctggtatcggcagtacagcggcaagagccccgagctgattatgttcatctacagcaa
cggcgacaaggaggacggccggttcaccgcccagctgaacaaggccagccagtatgtgagcctgctgatccgggacag
ccagcccagcgacagcgccacctacctgtgcgccgtgaacgacggcggcagactgaccttcggcgacggcaccaccct
gaccgtgaagcccaacatccagaaccccgacccgccgtgtaccagctgcgggacagcaagagcagcgacaagtctgt
gtgcctgttcaccgacttcgacagccagaccaatgtgagccagagcaaggacagcgacgtgtacatcaccgacaagacc
gtgctggacatgcggagcatggacttcaagagcaacagcgccgtggcctggagcaacaagagcgacttcgcctgcgcca
acgccttcaacaacagcatcatccccgaggacaccttttccccagccccgagagcagctgcgacgtgaaactggtggag
aagagcttcgagaccgacaccaacctgaacttccagaacctgagcgtgatcggcttcagaatcctgctgctgaaagtggct
gggttcaacctgctgatgaccctgcggctgtggagcagctaaacgcgt
(SEQ ID NO: 33)

Figure 12b

MEL c1 alpha protein sequence
MMKSLRVLLVILWLQLSWVWSQQKEVEQNSGPLSVPEGAIASLNCTYSDRGSQSFFWY
RQYSGKSPELIMFIYSNGDKEDGRFTAQLNKASQYVSLLIRDSQPSDSATYLCAVNDG
GRLTFGDGTTLTVKPNIQNPDPAVYQLRDSKSSDKSVCLFTDFDSQTNVSQSKDSDVY
ITDKTVLDMRSMDFKSNSAVAWSNKSDFACANAFNNSIIPEDTFFPSPESSCDVKLVE
KSFETDTNLNFQNLSVIGFRILLLKVAGFNLLMTLRLWSS
(SEQ ID NO: 34)

Figure 13a ctcgagccgccaccatgatgaagagcctgcgggtgctgctggtgatcctgtggctgcagctgagctgggtgtggagccag
cagaaggaggtggagcagaacagcggccccctgagcgtgcccgagggcgccatcgccagcctgaactgcacctacag
cgaccggggcagccagagcttcttctggtatcggcagtacagcggcaagagccccgagctgattatgttcatctacagcaa
cggcgacaaggaggacggccggttcaccgcccagctgaacaaggccagccagtatgtgagcctgctgatccgggacag
ccagcccagcgacagcgccacctacctgtgcgccgtgaacgacggcggcagaagcaccttcggcgacggcaccaccct
gaccgtgaagcccaacatccagaaccccgaccccgccgtgtaccagctgcgggacagcaagagcagcgacaagtctgt
gtgcctgttcaccgacttcgacagccagaccaatgtgagccagagcaaggacagcgacgtgtacatcaccgacaagacc
gtgctggacatgcggagcatggacttcaagagcaacagcgccgtggcctggagcaacaagagcgacttcgcctgcgcca
acgccttcaacaacagcatcatccccgaggacaccttttcccagccccgagagcagctgcgacgtgaaactggtggag
aagagcttcgagaccgacaccaacctgaacttccagaacctgagcgtgatcggcttcagaatcctgctgctgaaagtggct
gggttcaacctgctgatgaccctgcggctgtggagcagctaaacgcgt (SEQ ID NO: 35)

Figure 13b

MEL5 c1d alpha protein sequence
MMKSLRVLLVILWLQLSWVWSQQKEVEQNSGPLSVPEGAIASLNCTYSDRGSQSFFWY
RQYSGKSPELIMFIYSNGDKEDGRFTAQLNKASQYVSLLIRDSQPSDSATYLCAVNDG
GRSTFGDGTTLTVKPNIQNPDPAVYQLRDSKSSDKSVCLFTDFDSQTNVSQSKDSDVY
ITDKTVLDMRSMDFKSNSAVAWSNKSDFACANAFNNSIIPEDTFFPSPESSCDVKLVE
KSFETDTNLNFQNLSVIGFRILLLKVAGFNLLMTLRLWSS
(SEQ ID NO: 36)

Figure 14a ctcgagccgccaccatgatgaagagcctgcgggtgctgctggtgatcctgtggctgcagctgagctgggtgtggagccag
cagaaggaggtggagcagaacagcggccccctgagcgtgcccgagggcgccatcgccagcctgaactgcacctacag
cgaccggggcagccagagcttcttctggtatcggcagtacagcggcaagagccccgagctgattatgttcatctacagcaa
cggcgacaaggaggacggccggttcaccgcccagctgaacaaggccagccagtatgtgagcctgctgatccgggacag
ccagcccagcgacagcgccacctacctgtgcgccgtgaacgtgggcctgatcctgctgttcggcgacggcaccaccctga
ccgtgaagcccaacatccagaaccccgaccccgccgtgtaccagctgcgggacagcaagagcagcgacaagtctgtgtg
cctgttcaccgacttcgacagccagaccaatgtgagccagagcaaggacagcgacgtgtacatcaccgacaagaccgtgc
tggacatgcggagcatggacttcaagagcaacagcgccgtggcctggagcaacaagagcgacttcgcctgcgccaacgc
cttcaacaacagcatcatccccgaggacaccttttccccagccccgagagcagctgcgacgtgaaactggtggagaaga
gcttcgagaccgacaccaacctgaacttccagaacctgagcgtgatcggcttcagaatcctgctgctgaaagtggctgggtt
caacctgctgatgaccctgcggctgtggagcagctaaacgcgt
(SEQ ID NO: 37)

Figure 14b

MEL5 c9 alpha protein sequence
MMKSLRVLLVILWLQLSWVWSQQKEVEQNSGPLSVPEGAIASLNCTYSDRGSQSFFWY
RQYSGKSPELIMFIYSNGDKEDGRFTAQLNKASQYVSLLIRDSQPSDSATYLCAVNVG
LILLFGDGTTLTVKPNIQNPDPAVYQLRDSKSSDKSVCLFTDFDSQTNVSQSKDSDVY
ITDKTVLDMRSMDFKSNSAVAWSNKSDFACANAFNNSIIPEDTFFPSPESSCDVKLVE
KSFETDTNLNFQNLSVIGFRILLLKVAGFNLLMTLRLWSS
(SEQ ID NO: 38)

Figure 15a ggatccgccgccaccatgctgtgcagcctgctggccctgctgctgggcaccttcttcggagtgcggagccagaccatccac
cagtggcccgccacactggtgcagcctgtgggcagcccctgagcctggagtgcaccgtggagggcaccagcaacccc
aacctgtactggtatcggcaggccgcagggaggggggctgcagctgctgttctactctgtgggcatcggccagatcagcag
cgaggtgccccagaacctgagcgcctccaggccccaggaccggcagttcatcctgagcagcaagaagctgctgctgagc
gacagcggcttctacctgtgcgcctggagcgagaccggcctgggcaccggcgagctgttcttcggcgagggctccaggc
tgaccgtgctggaggacctgaagaacgtgttcccccccgaggtggccgtgttcgagcccagcgaggccgagatcagcca
cacccagaaggctaccctggtgtgtctggccaccggcttctaccccgaccacgtggagctgtcctggtgggtgaacggca
aggaggtgcacagcggcgtgtctaccgaccccagccctgaaggagcagcccgccctgaacgacagccggtactgcc
tgtcctccagactgagagtgagcgccaccttctggcagaaccccggaaccacttccggtgccaggtgcagttctacggcc
tgagcgagaacgacgagtggacccaggaccgggccaagcccgtgacccagattgtgagcgccgaggcctggggcaga
gccgactgcggcttcaccagcgagagctaccagcagggcgtgctgagcgccaccatcctgtacgagatcctgctgggca
aggccaccctgtacgccgtgctggtgtctgccctggtgctgatggctatggtgaagcggaaggacagccgggggctaagcg
gccgc
(SEQ ID NO: 39)

Figure 15b

MEL5 WT beta protein sequence
MLCSLLALLLGTFFGVRSQTIHQWPATLVQPVGSPLSLECTVEGTSNPNLYWYRQAAG
RGLQLLFYSVGIGQISSEVPQNLSASRPQDRQFILSSKKLLLSDSGFYLCAWSETGLG
TGELFFGEGSRLTVLEDLKNVFPPEVAVFEPSEAEISHTQKATLVCLATGFYPDHVEL
SWWVNGKEVHSGVSTDPQPLKEQPALNDSRYCLSSRLRVSATFWQNPRNHFRCQVQFY
GLSENDEWTQDRAKPVTQIVSAEAWGRADCGFTSESYQQGVLSATILYEILLGKATLY
AVLVSALVLMAMVKRKDSRG
(SEQ ID NO: 40)

Figure 17a atgatgaaatccttgagagttttactagtgatcctgtggcttcagttgagctgggtttggagccaacagaaggaggtggagca
gaattctggacccctcagtgttccagagggagccattgcctctctcaactgcacttacagtgaccgaggttcccagtccttctt
ctggtacagacaatattctgggaaaagccctgagttgataatgttcatatactccaatggtgacaaagaagatggaaggtttac
agcacagctcaataaagccagccagtatgtttctctgctcatcagagactcccagcccagtgattcagccacctacctctgtg
ccgtgaacgttgcaggcaaatcaacctttggggatgggactacgctcactgtgaagccaaatatccagaaccctgaccctg
ccgtgtaccagctgagagactctaaatccagtgacaagtctgtctgcctattcaccgattttgattctcaaacaaatgtgtcaca
aagtaaggattctgatgtgtatatcacagacaaaactgtgctagacatgaggtctatggacttcaagagcaacagtgctgtgg
cctggagcaacaaatctgactttgcatgtgcaaacgccttcaacaacagcattattccagaagacaccttcttccccagccca
gaaagttcctgtgatgtcaagctggtcgagaaaagctttgaaacagatacgaacctaaactttcaaaacctgtcagtgattgg
gttccgaatcctcctcctgaaagtggccgggtttaatctgctcatgacgctgcggctgtggtccagc
(SEQ ID NO: 44)

Figure 17b atgctctgctctctccttgcccttctcctgggcactttctttggggtcagatctcagactattcatcaatggccagcgaccctggt
gcagcctgtgggcagcccgctctctctggagtgcactgtggagggaacatcaaaccccaacctatactggtaccgacagg
ctgcaggcaggggcctccagctgctcttctactccgttggtattggccagatcagctctgaggtgccccagaatctctcagcc
tccagaccccaggaccggcagttcatcctgagttctaagaagctcctcctcagtgactctggcttctatctctgtgcctggtcc
gagacagggttaggcaccggggagctgttttttggagaaggctctaggctgaccgtactggaggacctgaaaaacgtgttc
ccacccgaggtcgctgtgtttgagccatcagaagcagagatctcccacacccaaaaggccacactggtgtgcctggccac
aggcttctaccccgaccacgtggagctgagctggtgggtgaatgggaaggaggtgcacagtggggtcagcacagacccg
cagcccctcaaggagcagcccgccctcaatgactccagatactgcctgagcagccgcctgagggtctcggccaccttctg
gcagaaccccgcaaccacttccgctgtcaagtccagttctacgggctctcggagaatgacgagtggacccaggataggg
ccaaacctgtcacccagatcgtcagcgccgaggcctggggtagagcagactgtggcttcacctccgagtcttaccagcaa
ggggtcctgtctgccaccatcctctatgagatcttgctagggaaggccaccttgtatgccgtgctggtcagtgccctcgtgct
gatggccatggtcaagagaaaggattccagaggc
(SEQ ID NO: 45)

Figure 18 atgatgaaatccttgagagttttactagtgatcctgtggcttcagttgagctgggtttggagccaacagaaggaggtggagca
gaattctggacccctcagtgttccagagggagccattgcctctctcaactgcacttacagtgaccgaggttcccagtccttctt
ctggtacagacaatattctgggaaaagccctgagttgataatgttcatatactccaatggtgacaaagaagatggaaggtttac
agcacagctcaataaagccagccagtatgtttctctgctcatcagagactcccagcccagtgattcagccacctacctctgtg
ccgtgaacgatgggggtcgtcttacctttggggatgggactacgctcactgtgaagccaaatatccagaaccctgaccctgc
cgtgtaccagctgagagactctaaatccagtgacaagtctgtctgcctattcaccgattttgattctcaaacaaatgtgtcacaa
agtaaggattctgatgtgtatatcacagacaaaactgtgctagacatgaggtctatggacttcaagagcaacagtgctgtggc
ctggagcaacaaatctgactttgcatgtgcaaacgccttcaacaacagcattattccagaagacaccttcttccccagcccag
aaagttcctgtgatgtcaagctggtcgagaaaagctttgaaacagatacgaacctaaactttcaaaacctgtcagtgattgggt
tccgaatcctcctcctgaaagtggccgggtttaatctgctcatgacgctgcggctgtggtccagc
(SEQ ID NO: 46)

Figure 20

M Q K E V E Q N S G P L S V P E G A I A S L N C T Y S <u>F Q</u>
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 47)

M Q K E V E Q N S G P L S V P E G A I A S L N C T Y S <u>F L</u>
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 48)

M Q K E V E Q N S G P L S V P E G A I A S L N C T Y S <u>Y Q</u>
G <u>A</u> Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 49)

M Q K E V E Q N S G P L S V P E G A I A S L N C T Y S <u>S I</u>
<u>H A</u> Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 50)

M Q K E V E Q N S G P L S V P E G A I A S L N C T Y S <u>N L</u>
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 51)

M Q K E V E Q N S G P L S V P E G A I A S L N C T Y S D <u>F</u>
G <u>A</u> Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P
(SEQ ID NO: 52)

Figure 20 (Cont.)

M Q K E V E Q N S G P L S V P E G A I A S L N C T Y S D R
G S Q S F F W Y R Q Y S G K S P E L I M F T̲ Y R̲ E̲ G D K E
D G R F T A Q L N K A S Q H̲ V S L L I R D S̲ Q P S D S A T
Y L C A V N V A G K S T F G D G T T L T V K P
(SEQ ID NO: 53)

Figure 21

```
M S Q T I H Q W P A T L V Q P V G S P L S L E C T V E G T
S N P N L Y W Y R Q A A G R G P Q L L F Y Y G P F G Q I S
S E V P Q N L S A S R P Q D R Q F I L S S K K L L L S D S
G F Y L C A W S E T G L G T G E L F F G E G S R L T V L
```
(SEQ ID NO: 54)

```
M S Q T I H Q W P A T L V Q P V G S P L S L E C T V E G T
S N P N L Y W Y R Q A A G R G P Q L L F Y F G P F G Q I S
S E V P Q N L S A S R P Q D R Q F I L S S K K L L L S D S
G F Y L C A W S E T G L G T G E L F F G E G S R L T V L
```
(SEQ ID NO: 55)

```
M S Q T I H Q W P A T L V Q P V G S P L S L E C T V E G T
S N P N L Y W Y R Q A A G R G P Q L L F Y F G P Y G Q I S
S E A P Q N L S A S R P Q D R Q F I L S S K K L L L S D S
G F Y L C A W S E T G L G T G E L F F G E G S R L T V L
```
(SEQ ID NO: 56)

```
M S Q T I H Q W P A T L V Q P V G S P L S L E C T V E G T
S N P N L Y W Y R Q A A G R G P Q L L F Y W G P F G Q I S
S E V P Q N L S A S R P Q D R Q F I L S S K K L L L S D S
G F Y L C A W S E T G L G T G E L F F G E G S R L T V L
```
(SEQ ID NO: 57)

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G M G G W Q F G E G S R L T V L
```
(SEQ ID NO: 58)

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G M G G W S F G E G S R L T V L
```
(SEQ ID NO: 59)

Figure 21 (Cont.)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G M G G W A F G E G S R L T V L
(SEQ ID NO: 60)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G V G G W D F G E G S R L T V L
(SEQ ID NO: 61)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G V G G W E F G E G S R L T V L
(SEQ ID NO: 62)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F V L S S K K L L L S D S
G F Y L C A W S E T G L N T S G W F F G E G S R L T V L
(SEQ ID NO: 63)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L N T N G W F F G E G S R L T V L
(SEQ ID NO: 64)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L N L G G W F F G E G S R L T V L
(SEQ ID NO: 65)

Figure 21 (Cont.)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L <u>N V S G</u> W F F G E G S R L T V L
(SEQ ID NO: 66)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L <u>N T T G</u> W F F G E G S R L T V L
(SEQ ID NO: 67)

Figure 22

```
M Q K E V E Q N S G P L S V P E G A I A S L N C T Y S F Q
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P N I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S
```
(SEQ ID NO: 68)

```
M Q K E V E Q N S G P L S V P E G A I A S L N C T Y S F L
G S Q S F F W Y R Q Y S G K S P E L I M F I Y S N G D K E
D G R F T A Q L N K A S Q Y V S L L I R D S Q P S D S A T
Y L C A V N V A G K S T F G D G T T L T V K P N I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S
```
(SEQ ID NO: 69)

```
M Q K E V E Q N S G P L S V P E G A I A S L N C T Y S D R
G S Q S F F W Y R Q Y S G K S P E L I M F T Y R E G D K E
D G R F T A Q L N K A S Q H V S L L I R D S Q P S D S A T
Y L C A V N V A G K S T F G D G T T L T V K P N I Q N P D
P A V Y Q L R D S K S S D K S V C L F T D F D S Q T N V S
Q S K D S D V Y I T D K C V L D M R S M D F K S N S A V A
W S N K S D F A C A N A F N N S I I P E D T F F P S P E S
S
```
(SEQ ID NO: 70)

Figure 23

```
M S Q T I H Q W P A T L V Q P V G S P L S L E C T V E G T
S N P N L Y W Y R Q A A G R G P Q L L F Y Y G P F G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID NO: 71)

```
M S Q T I H Q W P A T L V Q P V G S P L S L E C T V E G T
S N P N L Y W Y R Q A A G R G P Q L L F Y F G P F G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID NO: 72)

```
M S Q T I H Q W P A T L V Q P V G S P L S L E C T V E G T
S N P N L Y W Y R Q A A G R G P Q L L F Y F G P Y G Q I S
S E A P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID NO: 73)

Figure 23(Cont.)

M S Q T I H Q W P A T L V Q P V G S P L S L E C T V E G T
S N P N L Y W Y R Q A A G R G P Q L L F Y W G P F G Q I S
S E V P Q N L S A S R P Q D R Q F I L S S K K L L L S D S
G F Y L C A W S E T G L G T G E L F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
(SEQ ID NO: 74)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G M G G W Q F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
(SEQ ID NO: 75)

M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L G V G G W E F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
(SEQ ID NO: 76)

Figure 23(Cont.)

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L N L G G W F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID NO: 77)

```
M S Q T I H Q W P A T L V Q P V G S P L S L E C T V E G T
S N P N L Y W Y R Q A A G R G L Q L L F Y S V G I G Q I S
S E V P Q N L S A S R P Q D R Q F I L S S K K L L L S D S
G F Y L C A W S E T G L N V S G W F F G E G S R L T V L E
D L K N V F P P E V A V F E P S E A E I S H T Q K A T L V
C L A T G F Y P D H V E L S W W V N G K E V H S G V C T D
P Q P L K E Q P A L N D S R Y A L S S R L R V S A T F W Q
D P R N H F R C Q V Q F Y G L S E N D E W T Q D R A K P V
T Q I V S A E A W G R A D
```
(SEQ ID NO: 78)

HIGH AFFINITY MELAN-A T CELL RECEPTORS

This application is a national phase application of PCT/GB2006/001980 filed May 31, 2006, which was published in English under PCT Article 21(2) on Dec. 7, 2006 and which claims the benefit of GB0511124.0 filed Jun. 1, 2005.

The present invention relates to T cell receptors (TCRs) having the property of binding to AAGIGILTV-HLA-A*0201 and comprising at least one TCR α chain variable domain and/or at least one TCR β chain variable domain CHARACTERISED IN THAT said TCR has a $K_D$ for the said AAGIGILTV-HLA-A*0201 complex of less than or equal to 3 μM and/or an off-rate ($k_{off}$) of $1 \times 10^{-3}$ $S^{-1}$ or slower

BACKGROUND TO THE INVENTION

The AAGIGILTV peptide is derived from the Melan-A (Mart-1) protein that is expressed by the majority of fresh melanoma samples and approximately 60% of Melanoma cell lines, as well as normal melanocytes. ((Coulie et al., (1994) *J. Exp. Med.* 180: (1) 1-4) and Kawakami et al., (1994) *PNAS USA* 91: 3515) The Class I HLA molecules of these cancerous cells present peptides from this protein, including AAGIGILTV (SEQ ID NO: 43) (Melan-$A_{27-35}$). The AAGIGILTV-HLA-A*0201 complex appears to be an immuno-dominant target for Melanoma-specific T cells. ((Kawakami et al., (1994) *PNAS USA* 91: 3515) and (Rivoltini et al., (1995) *J Immunol* 154: 2257) Therefore, this peptide-HLA complex provides a cancer marker that TCRs can target, for example for the purpose of delivering cytotoxic or immuno-stimulatory agents to the cancer cells. However, for that purpose it would be desirable if the TCR had a higher affinity and/or a slower off-rate for the peptide-HLA complex than native TCRs specific for that complex.

BRIEF DESCRIPTION OF THE INVENTION

This invention makes available for the first time TCRs having high affinity ($K_D$) of the interaction less than or equal to 3 μM and/or an off-rate ($k_{off}$) of $1 \times 10^{-3}$ $S^{-1}$ or slower for the AAGIGILTV-HLA-A*0201 complex. Such TCRs are useful, either alone or associated with a therapeutic agent for targeting cancer cells presenting that complex.

DETAILED DESCRIPTION OF THE INVENTION

The present invention provides a T-cell receptor (TCR) having the property of binding to AAGIGILTV-HLA-A*0201 and comprising at least one TCR α chain variable domain and/or at least one TCR β chain variable domain CHARACTERISED IN THAT said TCR has a $K_D$ for the said AAGIGILTV-HLA-A*0201 complex of less than or equal to 3 μM and/or an off-rate ($k_{off}$) of $1 \times 10^{-3}$ $S^{-1}$ or slower.

In a further embodiment the present invention said TCRs have a $K_D$ for the AAGIGILTV-HLA-A*0201 complex of less than or equal to 1 μM.

The $K_D$ measurement can be made by any of the known methods. A preferred method is the Surface Plasmon Resonance (Biacore) method of Example 4.

For comparison, the interaction of a disulfide-linked soluble variant of the native MEL TCR (see SEQ ID NO: 9 for TCR α chain and SEQ ID NO: 10 for TCR β chain) and the AAGIGILTV-HLA-A*0201 complex has a $K_D$ of approximately 4 μM as measured by the Biacore-base method of Example 4.

The native MEL TCR specific for the AAGIGILTV-HLA-A*0201 complex has the following Valpha chain and Vbeta chain gene usage (using the terminology of the T cell receptor Factsbook, (2001) LeFranc and LeFranc, Academic Press, ISBN 0-12-441352-8, see below):

Alpha chain—TRAV 12-2
Beta chain:—TRBV 30

The native MEL TCR can be used as a template into which various mutations that impart high affinity and/or a slow off-rate for the interaction between TCRs of the invention and the AAGIGILTV-HLA-A*0201 complex can be introduced. Thus the invention includes TCRs which are mutated relative to the native MEL TCR α chain variable region (see FIG. 1a and SEQ ID No: 1) and/or β chain variable region (see FIG. 1b and SEQ ID NO: 2) in at least one complementarity determining region (CDR) and/or variable region framework region thereof. It is also contemplated that other hypervariable regions in the variable regions of the TCRs of the invention, such as the hypervariable 4 (HV4) regions, may be mutated so as to produce a high affinity mutant.

Native TCRs exist in heterodimeric αβ or γδ forms. However, recombinant TCRs consisting of a single TCR α or TCR β chain have previously been shown to bind to peptide MHC molecules.

In one embodiment the TCR of the invention comprise both an α chain variable domain and an TCR β chain variable domain.

As will be obvious to those skilled in the art the mutation(s) in the TCR α chain sequence and/or TCR β chain sequence may be one or more of substitution(s), deletion(s) or insertion(s). These mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see (Sambrook & Russell, (2001) Molecular Cloning—A Laboratory Manual ($3^{rd}$ Ed.) CSHL Press) Further information on LIC procedures can be found in (Rashtchian, (1995) *Curr Opin Biotechnol* 6 (1): 30-6). Phage display provides one means by which libraries of TCR variants can be generated. Methods suitable for the phage display and subsequent screening of libraries of TCR variants each containing a non-native disulfide interchain bond are detailed in (Li et al., (2005) *Nature Biotech* 23 (3): 349-354) and WO 2004/04404.

It should be noted that any αβ TCR that comprises similar Valpha and Vbeta gene usage and therefore amino acid sequence to that of the MEL TCR could make a convenient template TCR. It would then be possible to introduce into the DNA encoding one or both of the variable regions of the template αβ TCR the changes required to produce the mutated high affinity TCRs of the invention. As will be obvious to those skilled in the art, the necessary mutations could be introduced by a number of methods, for example site-directed mutagenesis.

Unless stated to the contrary, the TCR amino acid sequences herein are generally provided including an N-terminal methionine (Met or M) residue. As will be known to those skilled in the art this residue may be removed during the production of recombinant proteins. As will also be obvious to those skilled in the art, it may be possible to truncate the sequences provided at the C-terminus and/or N-terminus thereof, by 1, 2, 3, 4, 5 or more residues, without substantially affecting the pMHC binding characteristics of the TCR, all such trivial variants are encompassed by the present invention.

As used herein the term "variable region" is understood to encompass all amino acids of a given TCR which are not included within the constant domain as encoded by the TRAC gene for TCR α chains and either the TRBC1 or TRBC2 for TCR β chains. (T cell receptor Factsbook, (2001) LeFranc and LeFranc, Academic Press, ISBN 0-12-441352-8)

As used herein the term "variable domain" is understood to encompass all amino acids of a given TCR which are included within the amino acid sequence encoded by a TRAV gene for TCR α chains and a TRBV gene for TCR β chains. (T cell receptor Factsbook, (2001) LeFranc and LeFranc, Academic Press, ISBN 0-12-441352-8)

Embodiments of the invention include mutated TCRs which comprise mutation of one or more of alpha chain variable region amino acids corresponding to: 28D, 29R, 30G, 31S, 49M, 51I, 53S, 54N, 72Y, 94V, 95A, 96G, 97K, 98S, and 99T, for example the mutations corresponding to:
28D→F, 28D→Y, 28D→S, 28D→N,
29R→Q, 29R→L, 29RΘI, 29R→F,
30G→H,
31S→A,
49M→I,
51I→T,
53S→R,
54N→E,
72Y→H,
94V→D, 94V→P, 94V→S, 94V→L, 94V→N, 95A→G, 95A→S, 95A→E,
96G→N, 96G→P, 96G→V, 96G→M, 96G→L, 96G→R,
97K→R, 97K→Y, 97K→V, 97K→L, 97K→H, 97K→G, 97K→I, 97K→P,
98S→L, 98S→M, 98S→R,
99T→L or 99T→R The numbering used above is the same as that shown in FIG. 1a and SEQ ID No: 1

Embodiments of the invention include mutated TCRs which comprise mutation of one or more of beta chain variable region amino acids corresponding to: 45L, 51S, 52V, 53G, 54I, 76I, 100G, 101T, 102G, 103E, 104L and 105F, using the numbering shown in SEQ ID NO: 2 is/are mutated, for example the mutations corresponding to:
45L→P,
51S→Y, 51S→F, 51S→W,
52V→G,
53GP,
54I→F, 54-Y,
76I→V,
100G→N,
101T→M, 101T→L, 101T→V,
102G→S, 102G→N, 102G→T,
103E→G,
104L→W,
105F→S, 105F→A, 105F→Q, 105F→D or 105F→E The numbering used above is the same as that shown in FIG. 1b and SEQ ID No: 2

Further preferred embodiments of the invention are provided by TCRs comprising one of the mutated alpha chain variable region amino acid sequences shown in FIG. 6 (SEQ ID Nos: 11 to 24) or FIG. 20 (SEQ ID NOs: 47 to 53). Phenotypically silent variants of such TCRs also form part of this invention.

Further preferred embodiments of the invention are provided by TCRs comprising one of the mutated beta chain variable region amino acid sequences shown in FIG. 21 (SEQ ID Nos: 54 to 67). Phenotypically silent variants of such TCRs also form part of this invention.

Native TCRs exist in heterodimeric αβ or γδ forms. However, recombinant TCRs consisting of αα or ββ homodimers have previously been shown to bind to peptide MHC molecules. Therefore, one embodiment of the invention is provided by TCR αα or TCR ββ homodimers.

Further preferred embodiments are provided by TCRs of the invention comprising the alpha chain variable region amino acid sequence and the beta chain variable region amino acid sequence combinations listed below, phenotypically silent variants of such TCRs also form part of this invention:

| Alpha chain variable region sequence, SEQ ID NO: | Beta chain variable region sequence, SEQ ID NO: |
|---|---|
| 11 | 2 |
| 12 | 2 |
| 13 | 2 |
| 14 | 2 |
| 15 | 2 |
| 16 | 2 |
| 17 | 2 |
| 18 | 2 |
| 19 | 2 |
| 20 | 2 |
| 21 | 2 |
| 22 | 2 |
| 23 | 2 |
| 24 | 2 |
| 47 | 2 |
| 48 | 2 |
| 49 | 2 |
| 50 | 2 |
| 51 | 2 |
| 52 | 2 |
| 53 | 2 |
| 11 | 54 |
| 11 | 55 |
| 11 | 56 |
| 11 | 57 |
| 11 | 58 |
| 11 | 59 |
| 11 | 60 |
| 11 | 61 |
| 11 | 62 |
| 11 | 63 |
| 11 | 64 |
| 11 | 65 |
| 11 | 66 |
| 11 | 67 |

Preferred embodiments provide TCRs of the invention comprising:
the alpha chain variable region shown in the SEQ ID NO: 11 and the beta chain variable region shown in the SEQ ID NO: 2,
the alpha chain variable region shown in the SEQ ID NO: 47 and the beta chain variable region shown in the SEQ ID NO: 2.
the alpha chain variable region shown in the SEQ ID NO: 48 and the beta chain variable region shown in the SEQ ID NO: 2.
the alpha chain variable region shown in the SEQ ID NO: 53 and the beta chain variable region shown in the SEQ ID NO: 2.
the alpha chain variable region shown in the SEQ ID NO: 11 and the beta chain variable region shown in the SEQ ID NO: 54.
the alpha chain variable region shown in the SEQ ID NO: 11 and the beta chain variable region shown in the SEQ ID NO: 55.

the alpha chain variable region shown in the SEQ ID NO: 11 and the beta chain variable region shown in the SEQ ID NO: 56.

the alpha chain variable region shown in the SEQ ID NO: 11 and the beta chain variable region shown in the SEQ ID NO: 57.

the alpha chain variable region shown in the SEQ ID NO: 11 and the beta chain variable region shown in the SEQ ID NO: 58.

the alpha chain variable region shown in the SEQ ID NO: 11 and the beta chain variable region shown in the SEQ ID NO: 62.

the alpha chain variable region shown in the SEQ ID NO: 11 and the beta chain variable region shown in the SEQ ID NO: 65.

the alpha chain variable region shown in the SEQ ID NO: 11 and the beta chain variable region shown in the SEQ ID NO: 66.

Or phenotypically silent variants of any of the above TCRs.

In another preferred embodiment TCRs of the invention comprising the variable region combinations detailed above further comprise the alpha chain constant region amino acid sequence shown in FIG. 7a (SEQ ID NO: 25) and one of the beta chain amino acid constant region sequences shown in FIGS. 7b and 7c (SEQ ID NOs: 26 and 27) or phenotypically silent variants thereof.

As used herein the term "phenotypically silent variants" is understood to refer to those TCRs which have a $K_D$ for the said AAGIGILTV-HLA-A*0201 complex of less than or equal to 3 µM. For example, as is known to those skilled in the art, it may be possible to produce TCRs that incorporate minor changes in the constant and/or variable regions thereof compared to those detailed above without altering the affinity and/or off-rate for the interaction with the AAGIGILTV-HLA-A*0201 complex. Such trivial variants are included in the scope of this invention. Those TCRs in which one or more conservative substitutions have been made also form part of this invention.

In one broad aspect, the TCRs of the invention are in the form of either single chain TCRs (scTCRs) or dimeric TCRs (dTCRs) as described in WO 04/033685 and WO 03/020763.

A suitable scTCR form comprises a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

Alternatively the first segment may be constituted by an amino acid sequence corresponding to a TCR β chain variable region; the second segment may be constituted by an amino acid sequence corresponding to a TCR α chain variable region sequence fused to the N terminus of an amino acid sequence corresponding to a TCR α chain constant domain extracellular sequence The above scTCRs may further comprise a disulfide bond between the first and second chains, said disulfide bond being one which has no equivalent in native αβ T cell receptors, and wherein the length of the linker sequence and the position of the disulfide bond being such that the variable domain sequences of the first and second segments are mutually orientated substantially as in native αβ T cell receptors.

More specifically the first segment may be constituted by an amino acid sequence corresponding to a TCR α chain variable region sequence fused to the N terminus of an amino acid sequence corresponding to a TCR α chain constant domain extracellular sequence, the second segment may be constituted by an amino acid sequence corresponding to a TCR β chain variable region fused to the N terminus of an amino acid sequence corresponding to TCR β chain constant domain extracellular sequence, and a disulfide bond may be provided between the first and second chains, said disulfide bond being one which has no equivalent in native αβ T cell receptors.

In the above scTCR forms, the linker sequence may link the C terminus of the first segment to the N terminus of the second segment, and may have the formula -PGGG-(SGGGG)$_n$-P- wherein n is 5 or 6 and P is proline, G is glycine and S is serine.

(SEQ ID NO: 41)
-PGGG-SGGGGSGGGGSGGGGSGGGGSGGGG-P (SEQ ID NO: 42)
-PGGG-SGGGGSGGGGSGGGGSGGGGSGGGGSGGGG-P

A suitable dTCR form of the TCRs of the present invention comprises a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide bond which has no equivalent in native αβ T cell receptors.

The first polypeptide may comprise a TCR α chain variable region sequence is fused to the N terminus of a sequence corresponding to a TCR α chain constant domain extracellular sequence, and a second polypeptide wherein a sequence corresponding to a TCR β chain variable region sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof. ("TRAC" etc. nomenclature herein as per T cell receptor Factsbook, (2001) LeFranc and LeFranc, Academic Press, ISBN 0-12-441352-8)

The dTCR or scTCR form of the TCRs of the invention may have amino acid sequences corresponding to human αβ TCR extracellular constant and variable region sequences, and a disulfide bond may link amino acid residues of the said constant domain sequences, which disulfide bond has no equivalent in native TCRs. The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

Specific embodiments of the invention provided a TCR of the invention which is a dTCR comprising
a first polypeptide wherein a sequence corresponding to a TCR α chain variable region sequence is fused to the N terminus of a sequence corresponding to a TCR α chain constant domain extracellular sequence, and
a second polypeptide wherein a sequence corresponding to a TCR β chain variable region sequence fused to the N terminus a sequence corresponding to a TCR β chain constant domain extracellular sequence,
the first and second polypeptides being linked by a disulfide bond which has no equivalent in native αβ T cell between cysteine residues substituted for Thr 48 of exon 1 of TRAC*01 and Ser 57 of exon 1 of TRBC1*01 or TRBC2*01 or the non-human equivalent thereof.

In addition to the non-native disulfide bond referred to above, the dTCR or scTCR form of the TCRs of the invention may include a disulfide bond between residues corresponding to those linked by a disulfide bond in native TCRs.

The dTCR or scTCR form of the TCRs of the invention preferably does not contain a sequence corresponding to transmembrane or cytoplasmic sequences of native TCRs.

Currently preferred embodiments of the invention provide soluble TCRs comprising:
the alpha chain amino acid sequence of SEQ ID NO: 29 and beta chain amino acid sequence SEQ ID NO: 10.
the alpha chain amino acid sequence of SEQ ID NO: 68 and beta chain amino acid sequence SEQ ID NO: 10.
the alpha chain amino acid sequence of SEQ ID NO: 69 and beta chain amino acid sequence SEQ ID NO: 10.
the alpha chain amino acid sequence of SEQ ID NO: 70 and beta chain amino acid sequence SEQ ID NO: 10.
the alpha chain amino acid sequence of SEQ ID NO: 29 and beta chain amino acid sequence SEQ ID NO: 71.
the alpha chain amino acid sequence of SEQ ID NO: 29 and beta chain amino acid sequence SEQ ID NO: 72.
the alpha chain amino acid sequence of SEQ ID NO: 29 and beta chain amino acid sequence SEQ ID NO: 73.
the alpha chain amino acid sequence of SEQ ID NO: 29 and beta chain amino acid sequence SEQ ID NO: 74.
the alpha chain amino acid sequence of SEQ ID NO: 29 and beta chain amino acid sequence SEQ ID NO: 75.
the alpha chain amino acid sequence of SEQ ID NO: 29 and beta chain amino acid sequence SEQ ID NO: 76.
the alpha chain amino acid sequence of SEQ ID NO: 29 and beta chain amino acid sequence SEQ ID NO: 77.
the alpha chain amino acid sequence of SEQ ID NO: 29 and beta chain amino acid sequence SEQ ID NO: 78.

Also provided is a nucleic acid or nucleic acids encoding TCRs of the invention. Such a nucleic acid or nucleic acids may be provided in a form which has been adapted for expression in a prokaryote or eukaryote host cell. Suitable host cells include, but are not limited to, bacterial, yeast, mammalian or insect cells. For example, the host cell may be a human T cell or a human haematopoietic stem cell.

Such adapted nucleic acid or nucleic acids is/are mutated to reflect the codon preference of the host cell in to which it is introduced. The mutations introduced are silent mutations which do not affect the amino acid sequence of the polypeptide or polypeptides thereby encoded. GeneArt (Regensburg, Germany) offer a suitable nucleic acid optimisation service (GeneOptimizer™). WO 2004/059556, owned by GeneArt, provides further details of the optimisation process.

Further currently preferred embodiments of the invention are provided by nucleic acids consisting of one of the full-length TCR α chain DNA sequences of SEQ ID Nos 33, 35 or 37 (FIGS. 12a, 13a, or 14a, respectively) and the TCR β chain DNA sequence of SEQ ID No 39 (Shown in FIG. 15a). A nucleic acid complementary to any of the foregoing, or a corresponding RNA sequence also forms part of this invention. Furthermore, as will be obvious to those skilled in the art such nucleic acid or nucleic acids encoding TCRs of the invention may also comprise non-coding (intron) sequences.

The full-length wild-type and high affinity MEL TCR chain DNA sequences of SEQ ID Nos: 31, 33, 35, 37 and 39 encode the amino acid sequences of SEQ ID Nos: 32, 34, 36, 38, and 40 respectively. (FIGS. 11b, 12b, 13b, 14b and 15b respectively)

The amino acids sequences of SEQ ID Nos: 33, 35 and 37 comprise the high affinity MEL TCR alpha chain variable regions of SEQ ID Nos: 11, 15 and 23 respectively.

As will be obvious to those skilled in the art such full-length TCR chain DNA sequences encode for the following sequences:
A leader sequence and the extracellular, transmembrane, and cytoplasmic TCR sequences.

The full-length DNA sequences provided herein also include restriction enzyme recognition sequences to facilitate ligation into the vector of choice.

PEGylated TCR Monomers

In one particular embodiment a TCR of the invention is associated with at least one polyalkylene glycol chain(s). This association may be cause in a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably the complexes are water soluble, so the linker moiety should be selected accordingly. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their pharmaceutical suitability, for example their immunogenicity.

Examples of linker moieties which fulfil the above desirable criteria are known in the art, for example the art of linking antibody fragments.

There are two classes of linker that are preferred for use in the production of multivalent TCR molecules of the present invention. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

$$HOCH_2CH_2O(CH_2CH_2O)_n\text{—}CH_2CH_2OH$$

Wherein n is greater than two. However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the PK profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) Tumor Targetting 4 235-244) The size of the hydrophilic polymer used my in particular be selected on the basis of the intended therapeutic use of the TCR complex. Thus for example, where the product is intended to leave the circulation and penetrate tissue, for example for use in the treatment of a tumour, it may be advantageous to use low molecular weight polymers in the order of 5 $K_D$a. There are numerous review papers and books that detail the use of PEG and similar molecules in pharmaceutical formulations. For example, see Harris (1992) Polyethylene Glycol Chemistry—Biotechnical and Biomedical Applications, Plenum, New York, N.Y. or Harris & Zalipsky (1997) Chemistry and Biological Applications of Polyethylene Glycol ACS Books, Washington, D.C.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

—$(CH_2)_n$— wherein n=2 to 5

—$(CH_2)_3NHCO(CH_2)_2$

A TCR complex of the invention in which a divalent alkylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| TCR Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |
| TCR dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order TCR multimers | | |
| 15K, 3 arms, Mal$_3$ (for trimer) | Nektar | OJOONO3 |
| 20K, 4 arms, Mal$_4$ (for tetramer) | Nektar | OJOOPO4 |
| 40K, 8 arms, Mal$_8$ (for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
Vinyl sulfone
Benzotriazole carbonate
Succinimidyl proprionate
Succinimidyl butanoate
Thio-ester
Acetaldehydes
Acrylates
Biotin
Primary amines As stated above non-PEG based polymers also provide suitable linkers for multimerising the TCRs of the present invention. For example, moieties containing maleimide termini linked by aliphatic chains such as BMH and BMOE (Pierce, products Nos. 22330 and 22323) can be used.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, strepavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment. (Willuda et al. (2001) *J. Biol. Chem.* 276 (17): 14385-14392) Haemoglobin also has a tetramerisation domain that could potentially be used for this kind of application.

A multivalent TCR complex of the invention comprising at least two TCRs provides a final embodiment of this aspect, wherein at least one of said TCRs is associated with a therapeutic agent.

In one aspect a TCR (or multivalent complex thereof) of the present invention may alternatively or additionally comprise a reactive cysteine at the C-terminal or N-terminal of the alpha or beta chains thereof.

Diagnostic and Therapeutic Use

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains.

In one aspect the scTCR or one or both of the dTCR chains of TCRs of the present invention may be labelled with an detectable moiety, for example a label that is suitable for diagnostic purposes. Such labelled TCRs are useful in a method for detecting a AAGIGILTV-HLA-A*0201 complex which method comprises contacting the TCR ligand with a TCR (or a multimeric high affinity TCR complex) which is specific for the TCR ligand; and detecting binding to the TCR ligand. In tetrameric TCR complexes formed for example, using biotinylated heterodimers, fluorescent streptavidin can be used to provide a detectable label. Such a fluorescently-labelled TCR tetramer is suitable for use in FACS analysis, for example to detect antigen presenting cells carrying the AAGIGILTV-HLA-A*0201 complex for which these high affinity TCRs are specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant domains of the α and β chains, respectively.

In a further aspect a TCR (or multivalent complex thereof) of the present invention may alternatively or additionally be associated with (e.g. covalently or otherwise linked to) a therapeutic agent which may be, for example, a toxic moiety for use in cell killing, or an immune effector molecule such as an interleukin or a cytokine. A multivalent TCR complex of the invention may have enhanced binding capability for a TCR ligand compared to a non-multimeric wild-type or T cell receptor heterodimer of the invention. Thus, the multivalent TCR complexes according to the invention are particularly useful for tracking or targeting cells presenting particular antigens in vitro or in vivo, and are also useful as intermediates for the production of further multivalent TCR complexes having such uses. These TCRs or multivalent TCR complexes may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the AAGIGILTV-HLA-A*0201 complex and having the therapeutic agent associated therewith.

In particular, the soluble TCR or multivalent TCR complex of the present invention can be used to deliver therapeutic agents to the location of cells presenting a particular antigen. This would be useful in many situations and, in particular, against tumours.

A therapeutic agent could be delivered such that it would exercise its effect locally but not only on the cell it binds to. Thus, one particular strategy envisages anti-tumour molecules linked to TCRs or multivalent TCR complexes according to the invention specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Including but not limited to, ricin, diphtheria toxin, pseudomonas bacterial exotoxin A, DNAase and RNAase;

radio-nuclides, i.e. unstable isotopes of elements which decay with the concurrent emission of one or more of α or β particles, or γ rays. including but not limited to, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

prodrugs, including but not limited to, antibody directed enzyme pro-drugs;

immuno-stimulants, i.e. moieties which stimulate immune response. Including but not limited to, cytokines such as IL-2 and IFN, superantigens and mutants thereof, pHLA complexes and chemokines such as IL-8, platelet factor 4, melanoma growth stimulatory protein, etc, antibodies or fragments thereof, complement activators, xenogeneic protein domains, allogeneic protein domains, viral/bacterial protein domains, viral/bacterial peptides and anti-T cell determinant antibodies (e.g. anti-CD3 or anti-CD28).

Functional Antibody Fragments and Variants

Antibody fragments and variants/analogues which are suitable for use in the compositions and methods described herein include, but are not limited to, the following.

Antibody Fragments

As is known to those skilled in the art, it is possible to produce fragments of a given antibody which retain substantially the same binding characteristics as those of the parent antibody. The following provides details of such fragments:

Minibodies—These constructs consist of antibodies with a truncated Fc portion. As such they retain the complete binding domains of the antibody from which are derived.

Fab fragments—These comprise a single immunoglobulin light chain covalently-linked to part of an immunoglobulin heavy chain. As such, Fab fragments comprise a single antigen combining site. Fab fragments are defined by the portion of an IgG that can be liberated by treatment with papain. Such fragments are commonly produced via recombinant DNA techniques. (Reeves et al., (2000) *Lecture Notes on Immunology* (4th Edition) Published by Blackwell Science)

F(ab')$_2$ fragments—These comprise both antigen combining sites and the hinge region from a single antibody. F(ab')$_2$ fragments are defined by the portion of an IgG that can be liberated by treatment with pepsin. Such fragments are commonly produced via recombinant DNA techniques. (Reeves et al., (2000) *Lecture Notes on Immunology* (4th Edition) Published by Blackwell Science)

Fv fragments—These comprise an immunoglobulin variable heavy domain linked to an immunoglobulin variable light domain. A number of Fv designs have been produced. These include dsFvs, in which the association between the two domains is enhanced by an introduced disulfide bond. Alternatively, scFvs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. FV have also been multimerised to form diabodies and triabodies (Maynard et al., (2000) *Annu Rev Biomed Eng* 2 339-376)

Nanobodies™—These constructs, marketed by Ablynx (Belgium), comprise synthetic single immunoglobulin variable heavy domain derived from a camelid (e.g. camel or llama) antibody.

Domain Antibodies—These constructs, marketed by Domantis (Belgium), comprise an affinity matured single immunoglobulin variable heavy domain or immunoglobulin variable light domain.

Antibody Variants and Analogues

The defining functional characteristic of antibodies in the context of the present invention is their ability to bind specifically to a target ligand. As is known to those skilled in the art it is possible to engineer such binding characteristics into a range of other proteins. Examples of antibody variants and analogues suitable for use in the compositions and methods of the present invention include, but are not limited to, the following.

Protein scaffold-based binding polypeptides—This family of binding constructs comprise mutated analogues of proteins which contain native binding loops. Examples include Affibodies, marketed by Affibody (Sweden), which are based on a three-helix motif derived from one of the IgG binding domains of *Staphylococcus aureus* Protein A. Another example is provided by Evibodies, marketed by EvoGenix (Australia) which are based on the extracellular domains of CTLA-4 into which domains similar to antibody binding loops are grafted. A final example, Cytokine Traps marketed by Regeneron Pharmaceuticals (US), graft cytokine receptor domains into antibody scaffolds. (Nygren et al., (2000) *Current Opinion in Structural biology* 7:463-469) provides a review of the uses of scaffolds for engineering novel binding sites in proteins. This review mentions the following proteins as sources of scaffolds: CP1 zinc finger, Tendamistat, Z domain (a protein A analogue), PST1, Coiled coils, LACI-D1 and cytochrome $b_{562}$. Other protein scaffold studies have reported the use of Fibronectin, Green fluorescent protein (GFP) and ankyrin repeats.

As is known to those skilled in the art antibodies or fragments, variants or analogues thereof can be produced which bind to various parts of a given protein ligand. For example, anti-CD3 antibodies can be raised to any of the polypeptide chains from which this complex is formed (i.e. γ, δ, ε, ζ, and η CD3 chains) Antibodies which bind to the ε CD3 chain are the preferred anti-CD3 antibodies for use in the compositions and methods of the present invention.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

It is expected that the high affinity AAGIGILTV (SEQ ID NO: 43)-HLA-A*0201 specific TCRs disclosed herein may be used in methods for the diagnosis and treatment of cancer.

For cancer treatment, the localisation in the vicinity of tumours or metastasis would enhance the effect of toxins or immunostimulants. For vaccine delivery, the vaccine antigen could be localised in the vicinity of antigen presenting cells, thus enhancing the efficacy of the antigen. The method can also be applied for imaging purposes.

One embodiment is provided by an isolated cell presenting a TCR of the invention. For example, said cell may be a human T cell or a human haematopoietic stem cell Further embodiments of the invention are provided by a pharmaceutical composition comprising:

a TCR or a multivalent TCR complex of the invention (optionally associated with a therapeutic agent), or a plurality of cells presenting at least one TCR of the invention, or a nucleic acid or nucleic acids encoding a TCR of the invention together with a pharmaceutically acceptable carrier;

The invention also provides a method of treatment of cancer comprising administering to a subject suffering such cancer disease an effective amount of a TCR or a multivalent TCR complex of the invention (optionally associated with a therapeutic agent), or a plurality of cells presenting at least one TCR of the invention, or a nucleic acid or nucleic acids encoding a TCR of the invention. In a related embodiment the invention provides for the use of a TCR or a multivalent TCR complex of the invention (optionally associated with a therapeutic agent), or a plurality of cells presenting at least one TCR of the invention, or a nucleic acid or nucleic acids encoding a TCR of the invention in the preparation of a composition for the treatment of cancer.

As will be obvious to those skilled in the art, the cancers that are amenable to treatment by compositions comprising the TCRs of the invention will be Melan-A$^+$ cancers.

Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A scTCR or dTCR (which preferably is constituted by constant and variable sequences corresponding to human sequences) of the present invention may be provided in substantially pure form, or as a purified or isolated preparation. For example, it may be provided in a form which is substantially free of other proteins.

The invention also provides a method of identifying a high affinity TCR having the property of binding to AAGIGILTV-HLA-A*0201 CHARACTERISED IN THAT the TCR (i) comprises at least one TCR α chain variable domain and/or at least one TCR β chain variable domain and (ii) has a $K_D$ for the said AAGIGILTV-HLA-A*0201 complex of less than 3 μM said method comprising:
  (a) the production of a diverse library of TCRs comprising the α and β chain variable domains of the MEL TCR wherein one or both of the α and β chain variable domains comprise a mutation(s);
  (b) contacting said diverse library of TCRs with AAGIGILTV-HLA-A*0201 under conditions suitable to allow the binding of the TCRs to AAGIGILTV-HLA-A*0201; and
  (c) measuring the $K_D$ of the interaction.

Preferred features of each aspect of the invention are as for each of the other aspects *mutatis mutandis*. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIGS. 1a and 1b provide the alpha chain variable region amino acid and beta chain variable region amino acid sequences of the native MEL TCR respectively.

FIGS. 2a and 2b provide respectively the DNA sequence of soluble versions of the native MEL TCR α and β chains.

FIGS. 3a and 3b provide respectively the MEL TCR α and β chain extracellular amino acid sequences produced from the DNA sequences of FIGS. 2a and 2b.

FIGS. 4a and 4b provide respectively the DNA sequence of soluble versions of the MEL TCR α and β chains mutated to include additional cysteine residues to form a non-native disulphide bond. The mutated codon in each chain is indicated by shading and the introduced restriction enzyme recognition sites are underlined.

FIGS. 5a and 5b show respectively the MEL TCR α and β chain extracellular amino acid sequences produced from the DNA sequences of FIGS. 4a and 4b. The introduced cysteine in each chain is indicated by shading.

FIG. 6 provides the alpha chain variable region amino acid sequences of high affinity MEL TCR variants. The mutated residues are underlined FIG. 7a provides the amino acid sequence of a truncated form of TRAC.

FIG. 7b provides the amino acid sequence of a truncated form of TRBC1.

FIG. 7c provides the amino acid sequence of a truncated form of TRBC2.

FIG. 8a provides the plasmid map of the pEX202 plasmid.

FIG. 8b provides the DNA sequence of the pEX202 plasmid.

FIG. 9a details the alpha chain amino acid sequences of a preferred soluble high affinity MEL TCR variant.

FIG. 9b details the beta chain amino acid sequences of the wild-type soluble MEL TCR using the TRBC2 encoded constant region fused via a peptide linker to wild-type human IL-2. The linker and IL-2 sequences are in italics.

Figure 10:
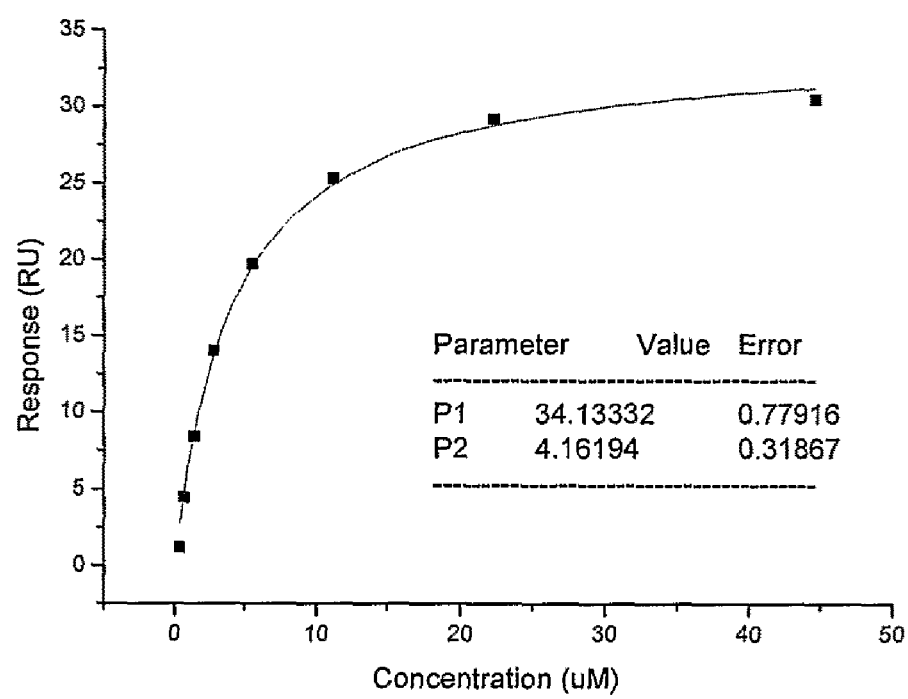

FIG. 10 provides the Biacore response curve generated for the interaction of a wild-type soluble disulfide-linked MEL TCR and HLA-AAGIGILTV-HLA-A*0201

FIGS. 11a and 11b provide the full-length wild-type MEL TCR alpha chain DNA sequence mutated in order to produce enhanced expression in human cells and the amino acid sequence thereby encoded respectively.

FIGS. 12a and 12b provide the full-length high affinity c1 MEL TCR alpha chain DNA sequence mutated in order to produce enhanced expression in human cells and the amino acid sequence thereby encoded respectively.

FIGS. 13a and 13b provide the full-length high affinity c1d MEL TCR alpha chain DNA sequence mutated in order to produce enhanced expression in human cells and the amino acid sequence thereby encoded respectively.

FIGS. 14a and 14b provide the full length high affinity c9 MEL TCR alpha chain sequence mutated in order to produce enhanced expression in human cells and the amino acid sequence thereby encoded respectively.

FIGS. 15a and 15b provide the full-length c9 MEL TCR alpha chain sequence mutated in order to produce enhanced expression in human cells and the amino acid sequence thereby encoded respectively.

Figure 16:
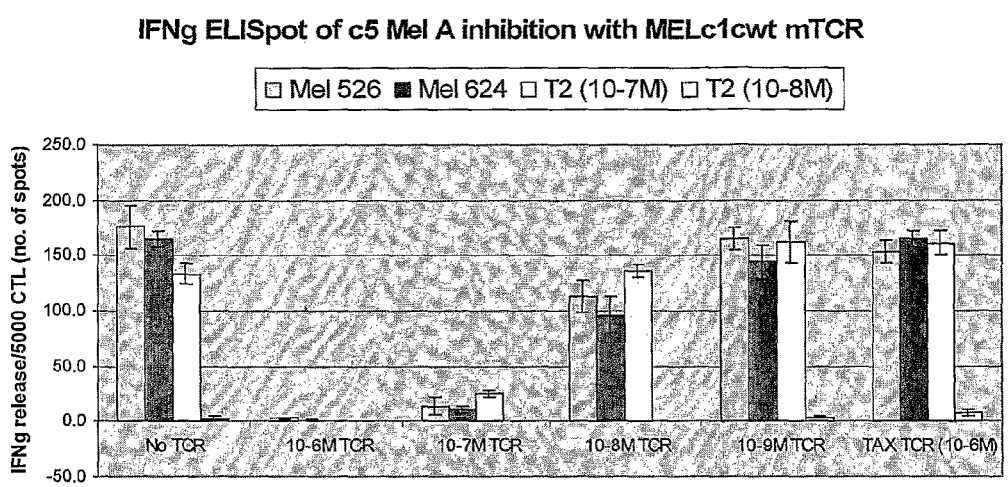

FIG. 16 Provides an ELISPOT assay demonstrating the ability of a soluble disulfide-linked version of the high affinity c1 WT Mel TCR to inhibit the activation of a Mel-specific CTL Clone.

FIGS. 17a and 17b provide the full-length wild-type MEL TCR alpha chain ORF encoding and wild-type MEL TCR beta chain ORF encoding DNA sequences respectively.

FIG. 18 provides the full-length c1 MEL TCR alpha chain ORF encoding DNA sequence comprising wild-type DNA codons except for those encoding the mutated amino acids.

Figure 19A:
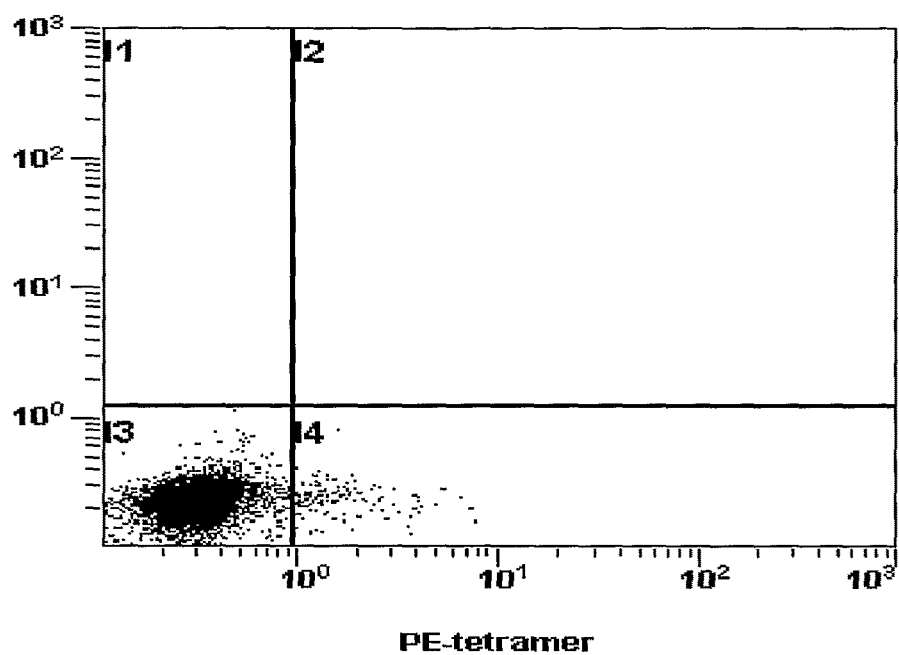

FIG. 19a provides FACS data on the level of TCR expression achieved by transfection of Jurkat cells with non-codon-optimised DNA encoding a c1 alpha/WT beta MEL TCR.

Figure 19B:
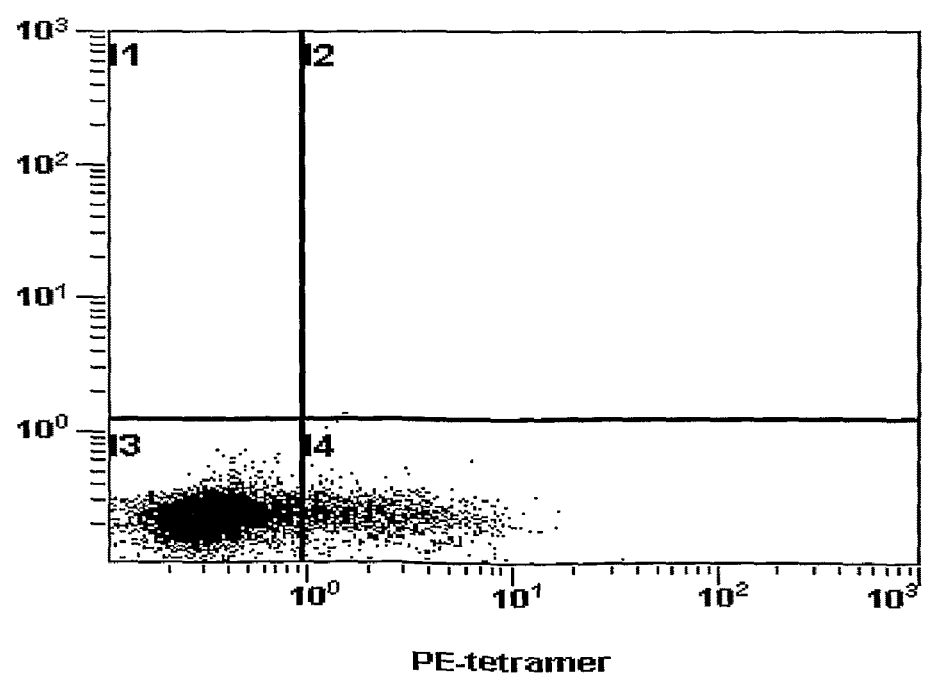

FIG. 19b provides FACS data on the level of TCR expression achieved by transfection of Jurkat cells with codon-optimised DNA encoding a c1 alpha/WT beta MEL TCR FIG. 20 provides the amino acid sequences of the variable regions of additional high affinity MEL TCR alpha chains. The mutated residues are underlined FIG. 21 provides the amino acid sequences of the variable regions of high affinity MEL TCR beta chains. The mutated residues are underlined FIG. 22 provides the amino acid sequences of soluble high affinity MEL TCR alpha chains comprising with a non-native cysteine residue. The non-native cysteine residue is highlighted and the mutated residues are underlined.

FIG. 23 provides the amino acid sequences of soluble high affinity MEL TCR beta chains comprising with a non-native cysteine residue. The non-native cysteine residue is highlighted and the mutated residues are underlined.

Example 1

Production of a Soluble Disulfide-Linked TCR Comprising the Native MEL Variable Domains FIGS. 4a and 4b provide the DNA sequences of soluble disulfide-linked alpha and beta chains from the wild-type MEL TCR which is specific for the AAGIGILTV-HLA-A*0201 complex. These DNA sequences can be synthesised de-novo by a number of contract research companies, for example GeneArt (Regensburg, Germany). Restriction enzyme recognition sites are also added to these DNA sequences in order to facilitate ligation of these DNA sequences into pGMT7-based expression plasmids, which contain the T7 promoter for high level expression in E. coli strain BL21-DE3 (pLysS) (Pan et al., Biotechniques (2000) 29 (6): 1234-8)

The DNA sequences encoding each TCR chain cut with NdeI and HindIII are ligated into separate pEX202 pGMT7-based vectors, which are also cut with NdeI and HindIII. (See FIG. 8a for the plasmid map of pEX202, and FIG. 8b for the DNA sequence of this vector (SEQ ID NO: 28))

Restriction enzyme recognition sites as introduced into DNA encoding the soluble wild-type MEL TCR chains:
NdeI—CATATG
HindIII—AAGCTT
Ligation Ligated plasmids are transformed into competent E. coli strain XL1-blue cells and plated out on LB/agar plates containing 100 mg/ml ampicillin. Following incubation overnight at 37° C., single colonies are picked and grown in 10 ml LB containing 100 mg/ml ampicillin overnight at 37° C. with shaking. Cloned plasmids are purified using a Miniprep kit (Qiagen) and the insert is sequenced using an automated DNA sequencer (Lark Technologies).

FIGS. 5a and 5b show respectively the soluble disulfide-linked wild-type MEL TCR α and β chain extracellular amino acid sequences produced from the DNA sequences of FIGS. 4a and 4b. The restriction enzyme recognition sequences in these DNA sequences are underlined.

Example 2

Production of High Affinity Variants of the Soluble Disulfide Linked MEL TCR

The soluble disulfide-linked native MEL TCR produced as described in Example 1 can be used a template from which to produce the TCRs of the invention which have an increased affinity for the AAGIGILTV (SEQ ID NO: 43)-HLA-A*0201 complex.

Phage display is one means by which libraries of HIV Gag TCR variants can be generated in order to identify high affinity mutants. For example, the TCR phage display and screening methods described in (Li et al., (2005) Nature Biotech 23 (3): 349-354) can be adapted and applied to HIV Gag TCRs.

The amino acid sequences of the mutated TCR alpha variable regions which, when combined with the wild-type MEL beta variable region, demonstrate high affinity for the AAGIGILTV-HLA-A*0201 complex are listed in FIG. 6. (SEQ ID Nos: 11-24) As is known to those skilled in the art the necessary codon changes required to produce these mutated chains can be introduced into the DNA encoding these chains by site-directed mutagenesis. (QuickChange™ Site-Directed Mutagenesis Kit from Stratagene)

Briefly, this is achieved by using primers that incorporate the desired codon change(s) and the pEX202 plasmids containing the relevant MEL TCR chain DNA as a template for the mutagenesis:

Mutagenesis is carried out using the following conditions: 50 ng plasmid template, 1 l of 10 mM dNTP, 5 μl of 10×Pfu DNA polymerase buffer as supplied by the manufacturer, 25 pmol of fwd primer, 25 pmol of rev primer, 1 μl pfu DNA polymerase in total volume 50 μl. After an initial denaturation step of 2 mins at 95 C, the reaction is subjected to 25 cycles of denaturation (95 C, 10 secs), annealing (55 C 10 secs), and elongation (72 C, 8 mins). The resulting product is digested with DpnI restriction enzyme to remove the template plasmid and transformed into E. coli strain XL1-blue. Mutagenesis was verified by sequencing.

Example 3

Expression, Refolding and Purification of Soluble TCR

The pEX202 expression plasmids containing the MEL TCR α-chains and MEL TCR β-chains as prepared in Examples 1 or 2 are transformed separately into E. coli strain BL21pLysS, and single ampicillin-resistant colonies are grown at 37° C. in TYP (ampicillin 100 μg/ml) medium to $OD_{600}$ of 0.4 before inducing protein expression with 0.5 mM IPTG. Cells are harvested three hours post-induction by centrifugation for 30 minutes at 400 rpm in a Beckman J-6B. Cell pellets are re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells are sonicated in 1 minute bursts for a total of around 10 minutes in a Milsonix XL2020 sonicator using a standard 12 mm diameter probe. Inclusion body pellets are recovered by centrifugation for 30 minutes at 13000 rpm in a Beckman J2-21 centrifuge. Three detergent washes are then carried out to remove cell debris and membrane components. Each time the inclusion body pellet is homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt is then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield is quantitated by solubilising with 6M guanidine-HCl and measurement with a Bradford dye-binding assay (PerBio).

Approximately 30 mg of TCR β chain and 60 mg of TCR α chain solubilised inclusion bodies are thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains is then injected into 1 litre of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) are added approximately 5 minutes before addition of the denatured TCR chains. The solution is left for 5 hrs±15 minutes. The refolded TCR is dialysed in Spectrapor 1 membrane (Spectrum; Product No. 132670) against 10 L 10 mM Tris pH 8.1 at 5° C.±3° C. for 18-20 hours. After this time, the dialysis buffer is changed to fresh 10 mM Tris pH 8.1 (10 L) and dialysis was continued at 5° C.±3° C. for another 20-22 hours.

sTCR is separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions are stored at 4° C. and analysed by Coomassie-stained SDS-PAGE before being pooled and concentrated. Finally, the sTCR is purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa is pooled and concentrated prior to characterisation by BIAcore surface plasmon resonance analysis.

Example 4

Biacore Surface Plasmon Resonance Characterisation of sTCR Binding to Specific pMHC A surface plasmon resonance biosensor (Biacore 3000™) was used to analyse the binding of a soluble MEL TCRs to the cognate peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Biotinylated class I HLA-A*0201 molecules were refolded in vitro from bacterially-expressed inclusion bodies containing the constituent subunit proteins and synthetic peptide, followed by purification and in vitro enzymatic biotinylation (O'Callaghan et al. (1999) Anal. Biochem. 266: 9-15). HLA-A*0201-heavy chain was expressed with a C-terminal biotinylation tag which replaces the transmembrane and cytoplasmic domains of the protein in an appropriate construct. Inclusion body expression levels of 75 mg/litre bacterial culture were obtained. The MHC light-chain or β2-microglobulin was also expressed as inclusion bodies in E. coli from an appropriate construct, at a level of ~500 mg/litre bacterial culture.

E. coli cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/litre heavy chain, 30 mg/litre β2 m into 0.4 M L-Arginine-HCl, 100 mM Tris pH 8.1, 3.7 mM cystamine, 6.6 mM β-cysteamine, 4 mg/ml of the AAGIG-ILTV peptide required to be loaded by the HLA-A*0201 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. HLA-A*0201-peptide complex eluted at approximately 250 mM NaCl, and peak fractions were collected, a cocktail of protease inhibitors (Calbiochem) was added and the fractions were chilled on ice.

Biotinylation tagged pMHC molecules were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 μg/ml BirA enzyme (purified according to O'Callaghan et al. (1999) Anal. Biochem. 266: 9-15). The mixture was then allowed to incubate at room temperature overnight.

The biotinylated pHLA-A*0201 molecules were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*0201 molecules were stored frozen at −20° C. Streptavidin was immobilised by standard amine coupling methods.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between soluble MEL TCRs containing a novel inter-chain bond and its cognate pMHC or an irrelevant pMHC combination, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2 m and streptavidin which have been chemically cross linked to the activated surface of the flow cells. The assay was then performed by passing sTCR over the surfaces of the different flow cells at a constant flow rate, measuring the SPR response in doing so.

To Measure Equilibrium Binding Constant

Serial dilutions of the wild-type or mutated MEL sTCR were prepared and injected at constant flow rate of 5 μl mini over two different flow cells; one coated with ~1000 RU of specific AAGIGILTV-HLA-A*0201 complex, the second coated with ~1000 RU of non-specific HLA-A2-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, *Principles and Problems in Physical Chemistry for Biochemists* (2$^{nd}$ Edition) 1979, Clarendon Press, Oxford).

To Measure Kinetic Parameters

For high affinity TCRs $K_D$ was determined by experimentally measuring the dissociation rate constant, kd, and the association rate constant, ka. The equilibrium constant $K_D$ was calculated as kd/ka.

TCR was injected over two different cells one coated with ~300 RU of specific HLA-A2-AAGIGILTV complex, the second coated with ~300 RU of non-specific HLA-A2-peptide complex. Flow rate was set at 50 µl/min. Typically 250 µl of TCR at ~3 µM concentration was injected. Buffer was then flowed over until the response had returned to baseline. Kinetic parameters were calculated using Biaevaluation software. The dissociation phase was also fitted to a single exponential decay equation enabling calculation of half-life.

Results

The interaction between a soluble disulfide-linked wild-type MEL TCR (consisting of the α and β TCR chains detailed in SEQ ID NOs 9 and 10 respectively) and the AAGIGILTV-HLA-A*0201 complex was analysed using the above methods and demonstrated a $K_D$ of 4 µM. (See FIG. 12 for Biacore response curve)

TCRs containing the variable region usage specified in the following table have a $K_D$ of less than or equal to 3 µM. Based on experience with high affinity TCRs other than the present MEL TCRs (see for example Li et al., *Nature Biotech* 2005 23 (3): 349-354) it is expected that some or all of the TCRs specified in the following table will have $k_{off}$ of $1 \times 10^{-3}$ S−1 or slower, and indeed that has been shown to be the case by the preparation of soluble TCRs comprising these variable domains. (See Table 1 below)

| Alpha chain variable region sequence, SEQ ID NO: | Beta chain variable region sequence, SEQ ID NO: |
|---|---|
| 11 | 2 |
| 12 | 2 |
| 13 | 2 |
| 14 | 2 |
| 15 | 2 |
| 16 | 2 |
| 17 | 2 |
| 18 | 2 |
| 19 | 2 |
| 20 | 2 |
| 21 | 2 |
| 22 | 2 |
| 23 | 2 |
| 24 | 2 |
| 47 | 2 |
| 48 | 2 |
| 49 | 2 |
| 50 | 2 |
| 51 | 2 |
| 52 | 2 |
| 53 | 2 |
| 11 | 54 |
| 11 | 55 |
| 11 | 56 |
| 11 | 57 |
| 11 | 58 |
| 11 | 59 |

-continued

| Alpha chain variable region sequence, SEQ ID NO: | Beta chain variable region sequence, SEQ ID NO: |
|---|---|
| 11 | 60 |
| 11 | 61 |
| 11 | 62 |
| 11 | 63 |
| 11 | 64 |
| 11 | 65 |
| 11 | 66 |
| 11 | 67 |

TABLE 1

Biacore data for the interaction of high affinity soluble disulfide-linked MEL TCRs comprising defined variable regions and the cognate AAGIGILTV-HLA-A*0201 peptide-MHC.

| Alpha chain variable region sequence SEQ ID NO: | Beta chain variable region sequence SEQ ID NO: | Affinity (KD) nM | Off-rate (Koff) 1/s |
|---|---|---|---|
| 11 | 2 | 6.4 | $3.26 \times 10^{-3}$ |
| 47 | 2 | 6.1 | $1.21 \times 10^{-3}$ |
| 48 | 2 | 3.2 | $6.56 \times 10^{-4}$ |
| 53 | 2 | 10.6 | $1.8 \times 10^{-3}$ |
| 11 | 54 | 0.42 | $2.3 \times 10^{-4}$ |
| 11 | 55 | 0.52 | $2.04 \times 10^{-3}$ |
| 11 | 56 | 0.82 | $2.2 \times 10^{-4}$ |
| 11 | 57 | 0.61 | $1.73 \times 10^{-4}$ |
| 11 | 58 | 0.40 | $1.55 \times 10^{-4}$ |
| 11 | 62 | 0.57 | $2.06 \times 10^{-4}$ |
| 11 | 65 | 1.0 | $1.14 \times 10^{-4}$ |
| 11 | 66 | 1.9 | $1.62 \times 10^{-4}$ |

Example 5

Production of a Soluble High Affinity MEL TCR-WT Human IL-2 Fusion Protein

The methods substantially as described in Examples 1 to 3 can be used to produce a soluble high affinity MEL TCR-WT human IL-2 fusion protein. Briefly, the DNA encoding the desired linker and WT human IL-2 are added into the 3' end of the DNA sequence of the soluble disulfide-linked wild-type MEL TCR beta chain immediately prior to the TAA ("Stop") codon. FIG. 9b provides the amino acid sequence of a fusion protein comprising a disulfide-linked wild-type MEL TCR beta chain fused to WT human IL-2 via linker sequence. (SEQ ID NO: 30) The linker and IL-2 portion of this fusion protein are indicated in italics. The DNA encoding this construct can then be ligated into pEX202. The soluble high affinity MEL TCR-IL-2 fusion protein can then be expressed by combining this beta chain fusion protein with a soluble high affinity disulfide-linked MEL TCR alpha chain containing any of the variable regions detailed in FIG. 6 (SEQ ID NOs: 11-24) using the methods substantially as described in Example 3. For example, FIG. 9a (SEQ ID NO: 29) provides the amino acid sequence of a soluble high affinity disulfide-linked MEL TCR alpha chain containing the variable region detailed in SEQ ID NO: 11.

Example 6

ELISPOT Assay for Assessing In-Vitro Inhibition of Cyto-Toxic T Cell (CTL) Activation by Soluble High Affinity Mel C1cWT Mel TCRs The following method provides a means of assessing the ability of Mel c1 cWT high affinity Mel TCRs to inhibit the activation AAGIGILTV-HLA-A*0201 reactive T cell clones.

The soluble Mel c1 cWT high affinity Mel TCR utilised in this experiment contained the Mel TCR alpha chain variable domain and WT Mel TCR beta chain variable regions of (SEQ ID NO: 11) and (SEQ ID NO: 2) respectively. The full amino acid sequences of the TCR alpha and beta chains of this soluble disulfide-linked TCR are provided by FIG. 9a (SEQ ID NO:29) and FIG. 5b (SEQ ID NO: 10) respectively.

Reagents:

Assay media: 10% FCS (heat-inactivated, Gibco, cat#10108-165), 88% RPMI 1640 (Gibco, cat#42401-018), 1% glutamine (Gibco, cat#25030-024) and 1% penicillin/streptomycin (Gibco, cat#15070-063).

Wash buffer: 0.01 M PBS/0.05% Tween 20 (1 sachet of Phosphate buffered saline with Tween 20, pH7.4 from Sigma, Cat. #P-3563 dissolved in 1 litre distilled water gives final composition 0.01 M PBS, 0.138 M NaCl, 0.0027 M KCl, 0.05% Tween 20).

PBS (Gibco, cat#10010-015).

Diaclone EliSpot kit (IDS) EliSpot kit contains all other reagents required i.e. capture and detection antibodies, skimmed milk powder, BSA, streptavidin-alkaline phosphatase, BCIP/NBT solution (Human IFN-γ PVDF Eli-spot 20×96 wells with plates (IDS cat#DC-856.051.020, DC-856.000.000.

The following method is based on the manufacturers instructions supplied with each kit but contains some alterations.

Method

100 μl capture antibody was diluted in 10 ml sterile PBS per plate. 100 μl diluted capture antibody was aliquoted into each well and left overnight at 4° C., or for 2 hr at room temperature. The plates were then washed three times with 450 μl wash buffer, Ultrawash 96-well plate washer, (Thermo Life Sciences) to remove excess capture antibody. 100 μl of 2% skimmed milk was then added to each well. (One vial of skimmed milk powder as supplied with the ELISPOT kit was dissolved in 50 ml sterile PBS). The plates were then incubated at room temperature for two hours before washing washed a further three times with 450 μl wash buffer, Ultrawash 96-well plate washer, (Thermo Life Sciences)

Mel 624 and Mel 526 target cancer cells were detached from their tissue culture flasks using trypsin, washed once by centrifugation (280×g for 10 minutes) in assay media and re-suspended at $1\times10^6$/ml in the same media. 50 ul of this suspension was then added to the assay plate to give a total target cell number of 50,000 cells/well.

ELAGIGILTV-pulsed T2 target cells were also used as a Control. This analogue peptide was used as it has a higher affinity for HLA-A*0201 than the WT peptide.

These peptide-pulsed cells were washed once by centrifugation (280×g for 10 minutes) in assay media and re-suspended at $1\times10^6$/ml in the same media. 50 ul of this suspension was then added to the assay plate to give a total target cell number of 50,000 cells/well.

A T cell clone (KA/C5) (effector cells), raised by autologous stimulation with the ELAGIGILTV peptide, was harvested by centrifugation (280×g for 10 min) and re-suspended at $1\times10^5$ cells/ml in assay media to give 5000 cells/well when 50 μl was added to the assay plate.

The soluble Mel c1 cWT high affinity Mel TCR high affinity Mel TCRs were diluted in assay media at a 3× concentration to give a 1× final when 50 ul was added to the plate in a final volume of 150 μl. The concentration range of high affinity Mel TCRs tested was 1 μM-1 nM.

Wells containing the following were then prepared, (the final reaction volume in each well was 100 μl):

Test Samples (Added in Order)
50 μl Mel 624 or Mel 526 target cells
50 ul of the desired concentration of soluble high affinity Mel c1 cWT TCRs.
50 ul KA/C5 T cell clone effector cells.
Negative Controls
50 μl target cells
50 ul of the highest concentration of soluble high affinity Mel c1 cWT TCRs.
50 μl assay media
And
50 μl effector cells
50 μl of the highest concentration soluble high affinity Mel c1 cWT TCRs
50 μl assay media
And
50 μl effector cells
50 μl target cells
50 μl of the highest concentration soluble of an irrelevant (HLA-A*0201-Tax-specific) high affinity mTCR
50 μl assay media
Positive Controls
50 μl Mel 624, Mel 526 or peptide-pulsed T2 target cells
50 μl effector cells
50 μl assay media The plates were then incubated overnight at 37° C./5% $CO_2$. The plates were then washed six times with wash buffer before tapping out excess buffer. 550 μl distilled water was then added to each vial of detection antibody supplied with the ELISPOT kit to prepare a diluted solution. 100 μl of the diluted detection antibody solution was then further diluted in 10 ml PBS/1% BSA per plate and 100 μl of the diluted detection antibody solution was aliquoted into each well. The plates were then incubated at room temperature for 90 minutes.

After this time the plates were washed three times with wash buffer (three times with 450 μl wash buffer, Ultrawash 96-well plate washer (Thermo Life Sciences) and tapped dry. 10 μl streptavidin-Alkaline phosphatase was then diluted with 10 ml with PBS/1% BSA per plate and 100 pt of the diluted streptavidin was added to each well and incubated at room temperature for 1 hr. The plates were then washed again three times with 450 μl wash buffer and tapped dry.

100 μl of the BCIP/NBT supplied solution was added to each well and the plates are covered in foil and left to develop for 5-15 min. The plates were checked regularly during this period for spot formation in order to decide when to terminate the reaction.

The plates were then washed thoroughly in tap water and shaken before being taken apart and left to dry on the bench.

Once dry the plates were read using an ELISPOT reader (Autoimmun Diagnostistika, Germany).

The number of spots that appeared in each well is proportional to the number of T cells activated. Therefore, any decrease in the number of spots in the wells containing the high affinity Mel TCR indicates inhibition of KA/C5 CTL Clone activation.

Results

As shown in FIG. 16 the soluble c1 cWT high affinity Mel TCRs were effective at inhibiting KA/C5 CTL clone activation. These data indicate that 100% inhibition of CTL activation was achieved using 1 M soluble c1 cWT high affinity Mel TCRs.

Example 7

Comparison of TCR Expression Levels on Jurkat Cells Transfected with Codon-Optimised and Non-Codon Optimised DNA Encoding a High Affinity (c1a WTP) MEL TCR $4 \times 10^6$ Jurkat cells grown in RMPI containing 10% heat-inactivated fetal calf serum medium cells were washed in serum-free medium and transfected with either:

a) 5 µg of endotoxin-free plasmid pCIneo containing the non-codon optimised sequence encoding MELα c1 mutant full length TCR chain plus 5 µg of endotoxin-free plasmid pCI containing the non-codon optimised sequence encoding MELβ wt full length TCR chain (The ORFs of these sequences are provided in FIG. 18 (SEQ ID NO: 46) and FIG. 17b (SEQ ID NO: 45) respectively); or b) 5 µg of endotoxin-free plasmid pCIneo containing an ORF codon-optimised MELα c1 mutant full length TCR chain plus 5 µg of endotoxin-free plasmid pCI containing an ORF codon-optimised MELβ wt full length TCR chain (The ORFs of these sequences are provided in FIG. 12a (SEQ ID NO: 33) and FIG. 15a (SEQ ID NO: 39) respectively).

Transfection was achieved by electroporation using 0.4 cm cuvettes using conditions of 0.27 kV and 975 µF in a BioRad Genepulser apparatus.

Cells were placed in 6 ml of RPMI containing 20% heat-inactivated fetal calf serum at 37 C for 72 hours.

Cells were stained in a volume of 100 µl PBS using 1 µl (0.54 µg) of PE-labelled streptavidin p/HLA-A2 tetramer (peptide was either heteroclytic MEL peptide ELAGIGILTV or a negative control NY-ESO peptide SLLMWITQC).

After 20 minutes at room temperature the cells were washed once in 5 ml RPMI and re-suspended in 800 µl RPMI and analysed on a FC500 Beckman Coulter instrument.

Results

FACs staining data shown in FIG. 19a and FIG. 19b are the level of cognate pMHC tetramer staining obtained for Jurkat cells transfected with the non-codon optimised and codon optimised DNA encoding the c1 alpha/WT beta MEL TCR. These data demonstrate that a high level of TCR surface expression was achieved using the codon optimised DNA compared to that achieved using the corresponding non-codon optimised DNA.

---

The invention claimed is:

1. An isolated T-cell receptor (TCR) having the property of binding to AAGIGILTV (SEQ ID NO:43)-HLA-A*0201 and comprising:
a TCR α chain variable domain having:
SEQ ID NO:1 or
SEQ ID NO:1 except that one or more of amino acids 28D, 29R, 30G, 31S, 49M, 51I, 53S, 54N, 72Y, 94V, 95A, 96G, 97K, 98S, and 99T is mutated; and
a TCR β chain variable domain having:
SEQ ID NO:2; or
SEQ ID NO:2 except that one or more of amino acids 45L, 51S, 52V, 53G, 54I, 76I, 100G, 101T, 102G, 103E, 104L, and 105F are mutated, said TCR having a $K_D$ for the said AAGIGILTV (SEQ ID NO:43)-HLA-A*0201 complex of less than or equal to 3 μM and/or an off-rate ($k_{off}$) of $1\times10^{-3}$ $S^{-1}$ or slower,
wherein the α and β chain variable domains of the TCR are not simultaneously unmutated SEQ ID NO:1 and unmutated SEQ ID NO:2, respectively.

2. A TCR as claimed in claim 1 comprising one or more alpha chain variable region mutations corresponding to 28D→F, 28D→Y, 28D→S, 28D→N, 29R→Q, 29R→L, 29R→I, 29R→F, 30G→H, 31S→A, 49M→I, 51I→T, 53S→R, 54N→E, 72Y→H, 94V→D, 94V→P, 94V→S, 94V→L, 94V→N, 95A→G, 95A→S, 95A→E, 9G6→N, 96G→P, 96G→V, 96G→M, 96G→L, 96G→R, 97K→R, 97K→Y, 97K→V, 97→L, 97K→H, 97K→G, 97K→I, 97K→P, 98S→L, 98S→M, 98S→R, 99T→L or 99T→R using the numbering shown in SEQ ID NO:1.

3. A TCR as claimed in claim 1 comprising one or more beta chain variable region mutations corresponding to 45L→P, 51S→Y, 51S→F, 51S→W, 52V→G, 53G→P, 54I→F, 54→Y, 7I6→V, 100G→N, 101T→M, 101T→L, 101T→V, 102G→S, 102G→N, 102G→T, 103E→G, 104L→W, 105F→S, 105F→A, 105F→Q, 105F→D, or 105F→E using the numbering shown in SEQ ID NO:2.

4. A TCR as claimed in claim 1 comprising one of the alpha chain variable region amino acid sequences of SEQ ID NOS: 11 to 24 or 47 to 53.

5. A TCR as claimed in claim 1 comprising one of the beta chain variable region amino acid sequences of SEQ ID NOS: 54 to 67.

6. A TCR as claimed in claim 1 comprising an alpha and beta chain variable region pairing selected from the group consisting of SEQ ID NOS:11 and 2; SEQ ID NOS:12 and 2; SEQ ID NOS:13 and 2; SEQ ID NOS:14 and 2; SEQ ID NOS:15 and 2; SEQ ID NOS:16 and 2; SEQ ID NOS:17 and 2; SEQ ID NOS:18 and 2; SEQ ID NOS:19 and 2; SEQ ID NOS:20 and 2; SEQ ID NOS:21 and 2; SEQ ID NOS:22 and 2; SEQ ID NOS:23 and 2; SEQ ID NOS:24 and 2; SEQ ID NOS:47 and 2; SEQ ID NOS:48 and 2; SEQ ID NOS:49 and 2; SEQ ID NOS:49 and 2; SEQ ID NOS:50 and 2; SEQ ID NOS:51 and 2; SEQ ID NOS:52 and 2; SEQ ID NOS:53 and 2; SEQ ID NOS:11 and 54; SEQ ID NOS:11 and 55; SEQ ID NOS:11 and 56; SEQ ID NOS:11 and 57; SEQ ID NOS:11 and 58; SEQ ID NOS:11 and 59; SEQ ID NOS:11 and 60; SEQ ID NOS:11 and 61; SEQ ID NOS:11 and 62; SEQ ID NOS:11 and 63; SEQ ID NOS:11 and 64; SEQ ID NOS:11 and 65; SEQ ID NOS:11 and 66; and SEQ ID NOS:11 and 67.

7. A TCR as claimed in claim 1 further comprising the alpha chain constant region amino acid sequence shown in SEQ ID NO:25 and/or one of the beta chain amino acid constant region sequences shown in SEQ ID NOS:26 and 27.

8. A TCR as claimed in claim 1 which is a dimeric T cell receptor (dTCR) or a single chain T cell receptor (scTCR).

9. A TCR as claimed in claim 1 wherein the TCR is associated with at least one polyalkylene glycol chain(s).

10. A TCR as claimed in claim 1 associated with a therapeutic agent or detectable moiety.

11. A TCR as claimed in claim 10 wherein the therapeutic agent or detectable moiety is covalently linked to the C terminus of one or both TCR chains.

12. A TCR as claimed in claim 10 associated with a therapeutic agent which is an immune effector molecule.

13. A TCR as claimed in claim 12 wherein the immune effector molecule is a cytokine.

14. A TCR as claimed in claim 12 wherein the immune effector molecule is IL-2, or a functional variant or fragment thereof.

15. A multivalent TCR complex comprising at least two TCRs as claimed in claim 1.

16. A pharmaceutical composition comprising:
a TCR as claimed in claim 1.

17. A recombinant T-cell receptor (TCR) having the property of binding to AAGIGILTV (SEQ ID NO:43)-HLA-A*0201 and comprising:
a TCR α chain variable domain having:
SEQ ID NO:1 or
SEQ ID NO:1 except that one or more of amino acids 28D, 29R, 30G, 31S, 49M, 51I, 53S, 54N, 72Y, 94V, 95A, 96G, 97K, 98S, and 99T is mutated; and
a TCR β chain variable domain having:
SEQ ID NO:2; or
SEQ ID NO:2 except that one or more of amino acids 45L, 51S, 52V, 53G, 54I, 76I, 100G, 101T, 102G, 103E, 104L, and 105F are mutated, said TCR having a $K_D$ for the said AAGIGILTV (SEQ ID NO:43)-HLA-A*0201 complex of less than or equal to 3 μM and/or an off-rate ($k_{off}$) of $1\times10^{-3}$ S$^{-1}$ or slower,
wherein the α and β chain variable domains of the TCR are not simultaneously unmutated SEQ ID NO:1 and unmutated SEQ ID NO:2, respectively.

18. A TCR as claimed in claim 17 comprising one or more alpha chain variable region mutations corresponding to 28D→F, 28D→Y, 28D→S, 28D→N, 29R→Q, 29R→L, 29R→I, 29R→F, 30G→H, 31S→A, 49M→I, 51I→T, 53S→R, 54N→E, 72Y→H, 94V→D, 94V→P, 94V→S, 94V→L, 94V→N, 95A→G, 95A→S, 95A→E, 9G6→N, 96G→P, 96G→V, 96G→M, 96G→L, 96G→R, 97K→R, 97K→Y, 97K→V, 97K→L, 97K→H, 97K→G, 97K→I, 97K→P, 98S→L, 98S→M, 98S→R, 99T→L or 99T→R using the numbering shown in SEQ ID NO:1.

19. A TCR as claimed in claim 17 comprising one or more beta chain variable region mutations corresponding to 45L→P, 51S→Y, 51S→F, 51S→W, 52V→G, 53G→P, 54I→F, 54→Y, 7I6→V, 100G→N, 101T→M, 101T→L, 101T→V, 102G→S, 102G→N, 102G→T, 103E→G, 104L→W, 105F→S, 105F→A, 105F→Q, 105F→D, or 105F→E using the numbering shown in SEQ ID NO:2.

20. A TCR as claimed in claim 17 comprising one of the alpha chain variable region amino acid sequences of SEQ ID NOS:11 to 24 or 47 to 53.

21. A TCR as claimed in claim 17 comprising one of the beta chain variable region amino acid sequences of SEQ ID NOS:54 to 67.

22. A TCR as claimed in claim 17 comprising an alpha and beta chain variable region pairing selected from the group consisting of SEQ ID NOS:11 and 2; SEQ ID NOS:12 and 2; SEQ ID NOS:13 and 2; SEQ ID NOS:14 and 2; SEQ ID NOS:15 and 2; SEQ ID NOS:16 and 2; SEQ ID NOS:17 and 2; SEQ ID NOS:18 and 2; SEQ ID NOS:19 and 2; SEQ ID NOS:20 and 2; SEQ ID NOS:21 and 2; SEQ ID NOS:22 and 2; SEQ ID NOS:23 and 2; SEQ ID NOS:24 and 2; SEQ ID NOS:47 and 2; SEQ ID NOS:48 and 2; SEQ ID NOS:49 and 2; SEQ ID NOS:49 and 2; SEQ ID NOS:50 and 2; SEQ ID NOS:51 and 2; SEQ ID NOS:52 and 2; SEQ ID NOS:53 and 2; SEQ ID NOS:11 and 54; SEQ ID NOS:11 and 55; SEQ ID NOS:11 and 56; SEQ ID NOS:11 and 57; SEQ ID NOS:11 and 58; SEQ ID NOS:11 and 59; SEQ ID NOS:11 and 60; SEQ ID NOS:11 and 61; SEQ ID NOS:11 and 62; SEQ ID NOS:11 and 63; SEQ ID NOS:11 and 64; SEQ ID NOS:11 and 65; SEQ ID NOS:11 and 66; and SEQ ID NOS:11 and 67.

23. A TCR as claimed in claim 17 further comprising the alpha chain constant region amino acid sequence shown in SEQ ID NO:25 and/or one of the beta chain amino acid constant region sequences shown in SEQ ID NOS:26 and 27.

24. A TCR as claimed in claim 17 which is a dimeric T cell receptor (dTCR) or a single chain T cell receptor (scTCR).

25. A TCR as claimed in claim 17 wherein the TCR is associated with at least one polyalkylene glycol chain(s).

26. A TCR as claimed in claim 17 associated with a therapeutic agent or detectable moiety.

27. A TCR as claimed in claim 26 wherein the therapeutic agent or detectable moiety is covalently linked to the C terminus of one or both TCR chains.

28. A TCR as claimed in claim 26 associated with a therapeutic agent which is an immune effector molecule.

29. A TCR as claimed in claim 28 wherein the immune effector molecule is a cytokine.

30. A TCR as claimed in claim 28 wherein the immune effector molecule is IL-2, or a functional variant or fragment thereof.

31. A multivalent TCR complex comprising at least two TCRs as claimed in claim 17.

32. A pharmaceutical composition comprising:
a TCR as claimed in claim 17.

33. An engineered T-cell receptor (TCR) having the property of binding to AAGIGILTV (SEQ ID NO:43)-HLA-A*0201 and comprising:
a TCR α chain variable domain having:
SEQ ID NO:1 or
SEQ ID NO:1 except that one or more of amino acids 28D, 29R, 30G, 31S, 49M, 51I, 53S, 54N, 72Y, 94V, 95A, 96G, 97K, 98S, and 99T is mutated; and
a TCR β chain variable domain having:
SEQ ID NO:2; or
SEQ ID NO:2 except that one or more of amino acids 45L, 51S, 52V, 53G, 54I, 76I, 100G, 101T, 102G, 103E, 104L, and 105F are mutated, said TCR having a $K_D$ for the said AAGIGILTV (SEQ ID NO:43)-HLA-A*0201 complex of less than or equal to 3 μM and/or an off-rate ($k_{off}$) of $1\times10^{-3}$ S$^{-1}$ or slower,
wherein the α and β chain variable domains of the TCR are not simultaneously unmutated SEQ ID NO:1 and unmutated SEQ ID NO:2, respectively.

34. A TCR as claimed in claim 33 comprising one or more alpha chain variable region mutations corresponding to 28D→F, 28D→Y, 28D→S, 28D→N, 29R→Q, 29R→L, 29R→I, 29R→F, 30G→H, 31S→A, 49M→I, 51I→T, 53S→R, 54N→E, 72Y→H, 94V→D, 94V→P, 94V→S, 94V→L, 94V→N, 95A→G, 95A→S, 95A→E, 9G6→N, 96G→P, 96G→V, 96G→M, 96G→L, 96G→R, 97K→R, 97K→Y, 97K→V, 97K→L, 97K→H, 97K→G, 97K→I, 97K→P, 98S→L, 98S→M, 98S→R, 99T→L or 99T→R using the numbering shown in SEQ ID NO:1.

35. A TCR as claimed in claim 33 comprising one or more beta chain variable region mutations corresponding to 45L→P, 51S→Y, 51S→F, 51S→W, 52V→G, 53G→P, 54I→F, 54→Y, 7I6→V, 100G→N, 101T→M, 101T→L, 101T→V, 102G→S, 102G→N, 102G→T, 103E→G, 104L→W, 105F→S, 105F→A, 105F→Q, 105F→D, or 105F→E using the numbering shown in SEQ ID NO:2.

36. A TCR as claimed in claim 33 comprising one of the alpha chain variable region amino acid sequences of SEQ ID NOS:11 to 24 or 47 to 53.

37. A TCR as claimed in claim 33 comprising one of the beta chain variable region amino acid sequences of SEQ ID NOS:54 to 67.

38. A TCR as claimed in claim 33 comprising an alpha and beta chain variable region pairing selected from the group consisting of SEQ ID NOS:11 and 2; SEQ ID NOS:12 and 2; SEQ ID NOS:13 and 2; SEQ ID NOS:14 and 2; SEQ ID NOS:15 and 2; SEQ ID NOS:16 and 2; SEQ ID NOS:17 and 2; SEQ ID NOS:18 and 2; SEQ ID NOS:19 and 2; SEQ ID NOS:20 and 2; SEQ ID NOS:21 and 2; SEQ ID NOS:22 and 2; SEQ ID NOS:23 and 2; SEQ ID NOS:24 and 2; SEQ ID NOS:47 and 2; SEQ ID NOS:48 and 2; SEQ ID NOS:49 and 2; SEQ ID NOS:49 and 2; SEQ ID NOS:50 and 2; SEQ ID NOS:51 and 2; SEQ ID NOS:52 and 2; SEQ ID NOS:53 and 2; SEQ ID NOS:11 and 54; SEQ ID NOS:11 and 55; SEQ ID NOS:11 and 56; SEQ ID NOS:11 and 57; SEQ ID NOS:11 and 58; SEQ ID NOS:11 and 59; SEQ ID NOS:11 and 60; SEQ ID NOS:11 and 61; SEQ ID NOS:11 and 62; SEQ ID NOS:11 and 63; SEQ ID NOS:11 and 64; SEQ ID NOS:11 and 65; SEQ ID NOS:11 and 66; and SEQ ID NOS:11 and 67.

39. A TCR as claimed in claim 33 further comprising the alpha chain constant region amino acid sequence shown in SEQ ID NO:25 and/or one of the beta chain amino acid constant region sequences shown in SEQ ID NOS:26 and 27.

40. A TCR as claimed in claim 33 which is a dimeric T cell receptor (dTCR) or a single chain T cell receptor (scTCR).

41. A TCR as claimed in claim 33 wherein the TCR is associated with at least one polyalkylene glycol chain(s).

42. A TCR as claimed in claim 33 associated with a therapeutic agent or detectable moiety.

43. A TCR as claimed in claim 42 wherein the therapeutic agent or detectable moiety is covalently linked to the C terminus of one or both TCR chains.

44. A TCR as claimed in claim 42 associated with a therapeutic agent which is an immune effector molecule.

45. A TCR as claimed in claim 44 wherein the immune effector molecule is a cytokine.

46. A TCR as claimed in claim 44 wherein the immune effector molecule is IL-2, or a functional variant or fragment thereof.

47. A multivalent TCR complex comprising at least two TCRs as claimed in claim 33.

48. A pharmaceutical composition comprising:
a TCR as claimed in claim 33.

49. A soluble TCR comprising an alpha chain and beta chain pairing selected from the group consisting of: SEQ ID NOS:29 and 10; SEQ ID NOS:68 and 10; SEQ ID NOS:70 and 10; SEQ ID NOS:29 and 71; SEQ ID NOS:29 and 72; SEQ ID NOS:29 and 73; SEQ ID NOS:29 and 74; SEQ ID NOS:29 and 75; SEQ ID NOS:29 and 76; SEQ ID NOS:29 and 77; SEQ ID NOS:29 and 78; and SEQ ID NOS:29 and 79.

* * * * *

SEQUENCE LISTING

```
<160> NUMBER OF SEQ ID NOS: 78

<210> SEQ ID NO 1
<211> LENGTH: 110
<212> TYPE: PRT
<213> ORGANISM: Homo sapiens

<400> SEQUENCE: 1

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 2
<211> LENGTH: 115
<212> TYPE: PRT
<213> ORGANISM: Homo sapiens

<400> SEQUENCE: 2

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30
```

```
Asn Leu Tyr Trp Tyr Arg Gln Ala Ala Gly Arg Gly Leu Gln Leu Leu
         35                  40                  45

Phe Tyr Ser Val Gly Ile Gly Gln Ile Ser Glu Val Pro Gln Asn
     50                  55                  60

Leu Ser Ala Ser Arg Pro Gln Asp Arg Gln Phe Ile Leu Ser Ser Lys
 65                  70                  75                  80

Lys Leu Leu Leu Ser Asp Ser Gly Phe Tyr Leu Cys Ala Trp Ser Glu
                 85                  90                  95

Thr Gly Leu Gly Thr Gly Glu Leu Phe Phe Gly Glu Gly Ser Arg Leu
                100                 105                 110

Thr Val Leu
        115

<210> SEQ ID NO 3
<211> LENGTH: 621
<212> TYPE: DNA
<213> ORGANISM: Homo sapiens

<400> SEQUENCE: 3
atgcaaaaag aagttgaaca aaattctgga cccctcagtg ttccagaggg agccattgcc        60
tctctcaact gcacttacag tgaccgaggt tcccagtcct tcttctggta cagacaatat       120
tctgggaaaa gccctgagtt gataatgttc atatactcca atggtgacaa agaagatgga       180
aggtttacag cacagctcaa taaagccagc cagtatgttt ctctgctcat cagagactcc       240
cagcccagtg attcagccac ctacctctgt gccgtgaacg ttgcaggcaa atcaaccttt       300
ggggatggga ctacgctcac tgtgaagcca aatatccaga accctgaccc tgccgtgtac       360
cagctgagag actctaagtc gagtgacaag tctgtctgcc tattcaccga ttttgattct       420
caaacaaatg tgtcacaaag taaggattct gatgtgtata tcacagacaa aactgtgcta       480
gacatgaggt ctatggactt caagagcaac agtgctgtgg cctggagcaa caaatctgac       540
tttgcatgtg caaacgcctt caacaacagc attattccag aagcaccctt cttccccagc       600
ccagaaagtt cctaagcttg a                                                 621

<210> SEQ ID NO 4
<211> LENGTH: 744
<212> TYPE: DNA
<213> ORGANISM: Homo sapiens

<400> SEQUENCE: 4
atgtctcaga ctattcatca atggccagcg accctggtgc agcctgtggg cagcccgctc        60
tctctggagt gcactgtgga gggaacatca aaccccaacc tatactggta ccgacaggct       120
gcaggcaggg gcctccagct gctcttctac tccgttggta ttggccagat cagctctgag       180
gtgccccaga atctctcagc ctccagaccc caggaccggc agttcatcct gagttctaag       240
aagctcctcc tcagtgactc tggcttctat ctctgtgcct ggtccgagac agggttaggc       300
accggggagc tgttttttgg agaaggctct aggctgaccg tactggagga cctgaaaaac       360
gtgttcccac ccgaggtcgc tgtgtttgag ccatcagaag cagagatctc cacacccaa        420 aaggccacac tggtgtgcct ggccaccggt ttctaccccg accacgtgga gctgagctgg       480
tgggtgaatg gaaggaggt gcacagtggg gtcagcacag cccgcagcc cctcaaggag         540 cagcccgccc tcaatgactc cagatacgct ctgagcagcc gctgagggt ctcggccacc       600 ttctggcagg accccgcaa ccacttccgc tgtcaagtca gttctacgg gctctcggag         660 aatgacgagt ggacccagga tagggccaaa cccgtcaccc agatcgtcag cgccgaggcc       720
```
tggggtagag cagactaagc ttga          744

<210> SEQ ID NO 5
<211> LENGTH: 204
<212> TYPE: PRT
<213> ORGANISM: Homo sapiens

<400> SEQUENCE: 5

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 6
<211> LENGTH: 245
<212> TYPE: PRT
<213> ORGANISM: Homo sapiens

<400> SEQUENCE: 6

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 7
<211> LENGTH: 628
<212> TYPE: DNA
<213> ORGANISM: Artificial Sequence
<220> FEATURE:
<223> OTHER INFORMATION: DNA encoding a soluble Mel TCR alpha chain with
      an introduced Cys codon and restriction enzyme recogntion sites

<400> SEQUENCE: 7
tatacatatg caaaaagaag ttgaacaaaa ttctggaccc ctcagtgttc cagagggagc     60
cattgcctct ctcaactgca cttacagtga ccgaggttcc cagtccttct tctggtacag    120
acaatattct gggaaaagcc ctgagttgat aatgttcata tactccaatg gtgacaaaga    180
agatggaagg tttacagcac agctcaataa agccagccag tatgtttctc tgctcatcag    240
agactcccag cccagtgatt cagccaccta cctctgtgcc gtgaacgttg caggcaaatc    300
aacctttggg gatgggacta cgctcactgt gaagccaaat atccagaacc ctgaccctgc    360
cgtgtaccag ctgagagact ctaagtcgag tgacaagtct gtctgcctat tcaccgattt    420
tgattctcaa acaaatgtgt cacaaagtaa ggattctgat gtgtatatca cagacaaatg    480
tgtgctagac atgaggtcta tggacttcaa gagcaacagt gctgtggcct ggagcaacaa    540
atctgacttt gcatgtgcaa acgccttcaa caacagcatt attccagaag acaccttctt    600
ccccagccca gaaagttcct aagcttga                                       628

<210> SEQ ID NO 8
<211> LENGTH: 751
<212> TYPE: DNA
<213> ORGANISM: Artificial Sequence
<220> FEATURE:
<223> OTHER INFORMATION: DNA encoding a soluble Mel TCR beta chain with
      an introduced Cys codon and restriction enzyme recognition sites

<400> SEQUENCE: 8
tatacatatg tctcagacta ttcatcaatg gccagcgacc ctggtgcagc ctgtgggcag     60
cccgctctct ctggagtgca ctgtggaggg aacatcaaac cccaacctat actggtaccg    120
acaggctgca ggcaggggcc tccagctgct cttctactcc gttggtattg gccagatcag    180
ctctgaggtg ccccagaatc tctcagcctc agacccccag gaccggcagt tcatcctgag    240
ttctaagaag ctcctcctca gtgactctgg cttctatctc tgtgcctggt ccgagacagg    300
gttaggcacc ggggagctgt ttttggaga aggctctagg ctgaccgtac tggaggacct    360

-continued

```
gaaaaacgtg ttcccacccg aggtcgctgt gtttgagcca tcagaagcag agatctccca    420
cacccaaaag gccacactgg tgtgcctggc accggtttc taccccgacc acgtggagct     480
gagctggtgg gtgaatggga aggaggtgca cagtggggtc tgcacagacc cgcagccct     540 caaggagcag cccgccctca atgactccag atacgctctg agcagccgcc tgagggtctc    600
ggccaccttc tggcaggacc cccgcaacca cttccgctgt caagtccagt tctacgggct    660
ctcggagaat gacgagtgga cccaggatag ggccaaaccc gtcacccaga tcgtcagcgc    720
cgaggcctgg ggtagagcag actaagcttg a                                   751
```

<210> SEQ ID NO 9
<211> LENGTH: 204
<212> TYPE: PRT
<213> ORGANISM: Artificial Sequence
<220> FEATURE:
<223> OTHER INFORMATION: A soluble Mel TCR alpha chain with an introduced Cys residue

<400> SEQUENCE: 9

```
Met Gln Lys Glu Val Glu Gln Asn Ser Gly Pro Leu Ser Val Pro Glu
 1               5                  10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200
```

<210> SEQ ID NO 10
<211> LENGTH: 245
<212> TYPE: PRT
<213> ORGANISM: Artificial Sequence
<220> FEATURE:
<223> OTHER INFORMATION: A soluble Mel TCR beta chain with an introduced Cys residue

<400> SEQUENCE: 10

```
Met Ser Gln Thr Ile His Gln Trp Pro Ala Thr Leu Val Gln Pro Val
 1               5                  10                  15

Gly Ser Pro Leu Ser Leu Glu Cys Thr Val Glu Gly Thr Ser Asn Pro
```

```
                20                  25                  30
Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
        50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 11
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 11

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asp Gly Gly
                85                  90                  95

Arg Leu Thr Phe Gly Asp Gly Thr Thr Leu Thr Val Lys Pro
            100                 105                 110

<210> SEQ ID NO 12
<211> LENGTH: 110
<212> TYPE: PRT
```

-continued

```
<213> ORGANISM: Artificial Sequence
<220> FEATURE:
<223> OTHER INFORMATION: A high affinity Mel TCR alpha chain variable
      domain

<400> SEQUENCE: 12

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Gly Gly
                85                  90                  95

Arg Leu Thr Phe Gly Asp Gly Thr Thr Leu Thr Val Lys Pro
            100                 105                 110

<210> SEQ ID NO 13
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 13

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asp Ala Gly
                85                  90                  95

Arg Leu Thr Phe Gly Asp Gly Thr Thr Leu Thr Val Lys Pro
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 14

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45
```

```
Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asp Gly Gly
                85                  90                  95

Lys Leu Thr Phe Gly Asp Gly Thr Thr Leu Thr Val Lys Pro
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 15

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asp Gly Gly
                85                  90                  95

Arg Ser Thr Phe Gly Asp Gly Thr Thr Leu Thr Val Lys Pro
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 16

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Ile Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Gly Gly
                85                  90                  95

Tyr Leu Leu Phe Gly Asp Gly Thr Thr Leu Thr Val Lys Pro
            100                 105                 110

<210> SEQ ID NO 17
<211> LENGTH: 110
<212> TYPE: PRT
```

<213> ORGANISM: Artificial Sequence
<220> FEATURE:
<223> OTHER INFORMATION: A high affinity Mel TCR alpha chain variable
      domain

<400> SEQUENCE: 17

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Pro Gly Gly
                85                  90                  95

Val Leu Thr Phe Gly Asp Gly Thr Thr Leu Thr Val Lys Pro
            100                 105                 110

<210> SEQ ID NO 18
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 18

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Pro Gly Gly
                85                  90                  95

Leu Leu Thr Phe Gly Asp Gly Thr Thr Leu Thr Val Lys Pro
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 19

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
         50                  55                  60

Gln Leu Asn Lys Ala Ser Gln Tyr Val Ser Leu Ile Arg Asp Ser
 65                  70                  75                  80

Gln Pro Ser Asp Ser Ala Thr Tyr Leu Cys Ala Val Asn Ser Gly Asn
                 85                  90                  95

His Met Thr Phe Gly Asp Gly Thr Thr Leu Thr Val Lys Pro
                100                 105                 110

<210> SEQ ID NO 20
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 20

Met Gln Lys Glu Val Glu Gln Asn Ser Gly Pro Leu Ser Val Pro Glu
 1               5                  10                  15

Gly Ala Ile Ala Ser Leu Asn Cys Thr Tyr Ser Asp Arg Gly Ser Gln
                 20                  25                  30

Ser Phe Phe Trp Tyr Arg Gln Tyr Ser Gly Lys Ser Pro Glu Leu Ile
             35                  40                  45

Met Phe Ile Tyr Ser Asn Gly Asp Lys Glu Asp Gly Arg Phe Thr Ala
         50                  55                  60

Gln Leu Asn Lys Ala Ser Gln Tyr Val Ser Leu Ile Arg Asp Ser
 65                  70                  75                  80

Gln Pro Ser Asp Ser Ala Thr Tyr Leu Cys Ala Val Asn Leu Ser Pro
                 85                  90                  95

Gly Leu Thr Phe Gly Asp Gly Thr Thr Leu Thr Val Lys Pro
                100                 105                 110

<210> SEQ ID NO 21
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 21

Met Gln Lys Glu Val Glu Gln Asn Ser Gly Pro Leu Ser Val Pro Glu
 1               5                  10                  15

Gly Ala Ile Ala Ser Leu Asn Cys Thr Tyr Ser Asp Arg Gly Ser Gln
                 20                  25                  30

Ser Phe Phe Trp Tyr Arg Gln Tyr Ser Gly Lys Ser Pro Glu Leu Ile
             35                  40                  45

Met Phe Ile Tyr Ser Asn Gly Asp Lys Glu Asp Gly Arg Phe Thr Ala
         50                  55                  60

Gln Leu Asn Lys Ala Ser Gln Tyr Val Ser Leu Ile Arg Asp Ser
 65                  70                  75                  80

Gln Pro Ser Asp Ser Ala Thr Tyr Leu Cys Ala Val Asn Val Gly Val
                 85                  90                  95

Ile Leu Arg Phe Gly Asp Gly Thr Thr Leu Thr Val Lys Pro
                100                 105                 110

<210> SEQ ID NO 22
<211> LENGTH: 110
<212> TYPE: PRT

```
<213> ORGANISM: Artificial Sequence
<220> FEATURE:
<223> OTHER INFORMATION: A high affinity Mel TCR alpha chain variable
      domain

<400> SEQUENCE: 22

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asn Gly Met
                85                  90                  95

Pro Ser Thr Phe Gly Asp Gly Thr Thr Leu Thr Val Lys Pro
            100                 105                 110

<210> SEQ ID NO 23
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 23

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Gly Leu
                85                  90                  95

Ile Leu Leu Phe Gly Asp Gly Thr Thr Leu Thr Val Lys Pro
            100                 105                 110

<210> SEQ ID NO 24
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 24

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45
```

```
Met Phe Ile Tyr Ser Asn Gly Asp Lys Glu Asp Gly Arg Phe Thr Ala
 50                  55                  60
Gln Leu Asn Lys Ala Ser Gln Tyr Val Ser Leu Leu Ile Arg Asp Ser
 65                  70                  75                  80
Gln Pro Ser Asp Ser Ala Thr Tyr Leu Cys Ala Val Asn Ser Glu Arg
                 85                  90                  95
Pro Arg Thr Phe Gly Asp Gly Thr Thr Leu Thr Val Lys Pro
            100                 105                 110

<210> SEQ ID NO 25
<211> LENGTH: 47
<212> TYPE: PRT
<213> ORGANISM: Homo sapiens

<400> SEQUENCE: 25

Asn Ile Gln Asn Pro Asp Pro Ala Val Tyr Gln Leu Arg Asp Ser Lys
 1               5                  10                  15
Ser Ser Asp Lys Ser Val Cys Leu Phe Thr Asp Phe Asp Ser Gln Thr
                20                  25                  30
Asn Val Ser Gln Ser Lys Asp Ser Asp Val Tyr Ile Thr Asp Lys
            35                  40                  45

<210> SEQ ID NO 26
<211> LENGTH: 56
<212> TYPE: PRT
<213> ORGANISM: Homo sapiens

<400> SEQUENCE: 26

Glu Asp Leu Asn Lys Val Phe Pro Pro Glu Val Ala Val Phe Glu Pro
 1               5                  10                  15
Ser Glu Ala Glu Ile Ser His Thr Gln Lys Ala Thr Leu Val Cys Leu
                20                  25                  30
Ala Thr Gly Phe Phe Pro Asp His Val Glu Leu Ser Trp Trp Val Asn
            35                  40                  45
Gly Lys Glu Val His Ser Gly Val
         50                  55

<210> SEQ ID NO 27
<211> LENGTH: 56
<212> TYPE: PRT
<213> ORGANISM: Homo sapiens

<400> SEQUENCE: 27

Glu Asp Leu Lys Asn Val Phe Pro Pro Glu Val Ala Val Phe Glu Pro
 1               5                  10                  15
Ser Glu Ala Glu Ile Ser His Thr Gln Lys Ala Thr Leu Val Cys Leu
                20                  25                  30
Ala Thr Gly Phe Tyr Pro Asp His Val Glu Leu Ser Trp Trp Val Asn
            35                  40                  45
Gly Lys Glu Val His Ser Gly Val
         50                  55

<210> SEQ ID NO 28
<211> LENGTH: 3857
<212> TYPE: DNA
<213> ORGANISM: Artificial Sequence
<220> FEATURE:
<223> OTHER INFORMATION: DNA sequence of the pEX202 plasmid

<400> SEQUENCE: 28
gatctcgatc ccgcgaaatt aatacgactc actataggga gaccacaacg gtttccctct    60
```

```
agaaataatt ttgtttaact ttaagaagga gatatacata tgcagaagga agtggagcag    120
aactctggac ccctcagtgt tccagaggga gccattgcct ctctcaactg cacttacagt    180
gaccgaggtt cccagtcctt cttctggtac agacaatatt ctgggaaaag ccctgagttg    240
ataatgtcca tatactccaa tggtgacaaa gaagatggaa ggtttacagc acagctcaat    300
aaagccagcc agtatgtttc tctgctcatc agagactccc agcccagtga ttcagccacc    360
tacctctgtg ccgttacaac tgacagctgg gggaaattgc agtttggagc agggacccag    420
gttgtggtca ccccagatat ccagaaccct gaccctgccg tgtaccagct gagagactct    480
aaatccagtg acaagtctgt ctgcctattc accgattttg attctcaaac aaatgtgtca    540
caaagtaagg attctgatgt gtatatcaca gacaaaactg tgctagacat gaggtctatg    600
gacttcaaga gcaacagtgc tgtggcctgg agcaacaaat ctgactttgc atgtgcaaac    660
gccttcaaca cagcattat tccagaagac accttcttcc ccagcccaga aagttccccc    720
gggggtagaa tcgcccggct ggaggaaaaa gtgaaaacct gaaagctca gaactcggag    780 ctggcgtcca cggccaacat gctcagggaa caggtggcac agcttaaaca gaaagtcatg    840
aactactagg atccatggta agcttgaatt ccgatccggc tgctaacaaa gcccgaaagg    900
aagctgagtt ggctgctgcc accgctgagc aataactagc ataacccctt ggggcctcta    960
aacgggtctt gaggggtttt ttgctgaaag gaggaactat atccggataa ttcttgaaga    1020
cgaaagggcc tcgtgatacg cctatttta taggttaatg tcatgataat aatggtttct    1080
tagacgtcag gtggcacttt tcggggaaat gtgcgcggaa cccctatttg tttattttc    1140 taaatacatt caaatatgta tccgctcatg agacaataac cctgataaat gcttcaataa    1200
tattttgtta aaattcgcgt taaattttg ttaaatcagc tcattttta accaataggc    1260 cgaaatcggc aaaatccctt ataaatcaaa agaatagacc gagatagggt tgagtgttgt    1320
tccagttggg aacaagagtc cactattaaa gaacgtggac tccaacgtca agggcgaaa    1380 aaccgtctat cagggcgatg gcccactacg tgaaccatca ccctaatcaa gttttttggg    1440
gtcgaggtgc cgtaaagcac taaatcggaa ccctaaaggg agccccgat ttagagcttg    1500 acggggaaag ccggcgaacg tggcgagaaa ggaagggaag aaagcgaaag gagcgggcgc    1560
tagggcgctg gcaagtgtag cggtcacgct gcgcgtaacc accacacccg ccgcgcttaa    1620
tgcgccgcta cagggcgcgt caggtggcac ttttcgggga aatgtgcgcg aaccccctat    1680
ttgtttattt ttctaaatac attcaaatat gtatccgctc atgagacaat aaccctgata    1740
aatgcttcaa taatattgaa aaaggaagag tatgagtatt caacatttcc gtgtcgccct    1800
tattcccttt tttgcggcat tttgccttcc tgttttgct cacccagaaa cgctggtgaa    1860
agtaaaagat gctgaagatc agttgggtgc acgagtgggt tacatcgaac tggatctcaa    1920
cagcggtaag atccttgaga ttttcgccc gaagaacgt tttccaatga tgagcacttt    1980
taaagttctg ctatgtggcg cggtattatc ccgtgttgac gccgggcaag agcaactcgg    2040
tcgccgcata cactattctc agaatgactt ggttgagtac tcaccagtca cagaaaagca    2100
tcttacggat ggcatgacag taagagaatt atgcagtgct gccataacca tgagtgataa    2160
cactgcggcc aacttacttc tgacaacgat cggaggaccg aaggagctaa ccgctttttt    2220
gcacaacatg ggggatcatg taactcgcct tgatcgttgg gaaccggagc tgaatgaagc    2280
cataccaaac gacgagcgtg acaccacgat gcctgcagca atggcaacaa cgttgcgcaa    2340
actattaact ggcgaactac ttactctagc ttcccggcaa caattaatag actggatgga    2400
ggcggataaa gttgcaggac cacttctgcg ctcggccctt ccggctggct ggtttattgc    2460
```

```
tgataaatct ggagccggtg agcgtgggtc tcgcggtatc attgcagcac tggggccaga    2520
tggtaagccc tcccgtatcg tagttatcta cacgacgggg agtcaggcaa ctatggatga    2580
acgaaataga cagatcgctg ataggtgc ctcactgatt aagcattggt aactgtcaga      2640
ccaagtttac tcatatatac tttagattga tttaaaactt cattttaat ttaaaaggat    2700 ctaggtgaag atccttttg ataatctcat gaccaaaatc ccttaacgtg agttttcgtt    2760
ccactgagcg tcagaccccg tagaaaagat caaaggatct tcttgagatc ctttttttct    2820
gcgcgtaatc tgctgcttgc aaacaaaaaa accaccgcta ccagcggtgg tttgtttgcc    2880
ggatcaagag ctaccaactc ttttccgaa ggtaactggc ttcagcagag cgcagatacc    2940
aaatactgtc cttctagtgt agccgtagtt aggccaccac ttcaagaact ctgtagcacc    3000
gcctacatac ctcgctctgc taatcctgtt accagtggct gctgccagtg gcgataagtc    3060
gtgtcttacc gggttggact caagacgata gttaccggat aaggcgcagc ggtcgggctg    3120
aacggggggt tcgtgcacac agcccagctt ggagcgaacg acctacaccg aactgagata    3180
cctacagcgt gagctatgag aaagcgccac gcttcccgaa gggagaaagg cggacaggta    3240
tccggtaagc ggcagggtcg aacaggaga gcgcacgagg gagcttccag ggggaaacgc    3300
ctggtatctt tatagtcctg tcgggtttcg ccacctctga cttgagcgtc gattttgtg    3360 atgctcgtca ggggggcgga gcctatggaa aaacgccagc aacgcggcct ttttacggtt    3420
cctggccttt tgctggcctt ttgctcacat gttctttcct gcgttatccc ctgattctgt    3480
ggataaccgt attaccgcct ttgagtgagc tgataccgct cgccgcagcc gaacgaccga    3540
gcgcagcgag tcagtgagcg aggaagcgga agagcgcctg atgcggtatt ttctccttac    3600
gcatctgtgc ggtatttcac accgcaatgg tgcactctca gtacaatctg ctctgatgcc    3660
gcatagttaa gccagtatac actccgctat cgctacgtga ctgggtcatg gctgcgcccc    3720
gacacccgcc aacacccgct gacgcgccct gacgggcttg tctgctcccg gcatccgctt    3780
acagacaagc tgtgaccgtc tccgggagct gcatgtgtca gaggttttca ccgtcatcac    3840
cgaaacgcgc gaggcag                                                   3857
```

<210> SEQ ID NO 29
<211> LENGTH: 204
<212> TYPE: PRT
<213> ORGANISM: Artificial Sequence
<220> FEATURE:
<223> OTHER INFORMATION: A soluble high affinity MEL TCR alpha chain

<400> SEQUENCE: 29

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Asp Gly Gly
                85                  90                  95

Arg Leu Thr Phe Gly Asp Gly Thr Thr Leu Thr Val Lys Pro Asn Ile
            100                 105                 110
```

```
Gln Asn Pro Asp Pro Ala Val Tyr Gln Leu Arg Asp Ser Lys Ser Ser
            115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
            195                 200

<210> SEQ ID NO 30
<211> LENGTH: 380
<212> TYPE: PRT
<213> ORGANISM: Artificial Sequence
<220> FEATURE:
<223> OTHER INFORMATION: Soluble MEL TCR soluble beta chain with an
      introduced Cys residue fused via a peptide linker to wild-type
      human IL-2

<400> SEQUENCE: 30

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Pro Gly Ala Pro Thr Ser Ser Ser Thr Lys Lys
                245                 250                 255

Thr Gln Leu Gln Leu Glu His Leu Leu Leu Asp Leu Gln Met Ile Leu
            260                 265                 270
```

```
Asn Gly Ile Asn Asn Tyr Lys Asn Pro Lys Leu Thr Arg Met Leu Thr
            275                 280                 285

Phe Lys Phe Tyr Met Pro Lys Ala Thr Glu Leu Lys His Leu Gln
        290                 295                 300

Cys Leu Glu Glu Glu Leu Lys Pro Leu Glu Glu Val Leu Asn Leu Ala
305                 310                 315                 320

Gln Ser Lys Asn Phe His Leu Arg Pro Arg Asp Leu Ile Ser Asn Ile
                325                 330                 335

Asn Val Ile Val Leu Glu Leu Lys Gly Ser Glu Thr Thr Phe Met Cys
            340                 345                 350

Glu Tyr Ala Asp Glu Thr Ala Thr Ile Val Glu Phe Leu Asn Arg Trp
        355                 360                 365

Ile Thr Phe Cys Gln Ser Ile Ile Ser Thr Leu Thr
        370                 375                 380

<210> SEQ ID NO 31
<211> LENGTH: 839
<212> TYPE: DNA
<213> ORGANISM: Artificial Sequence
<220> FEATURE:
<223> OTHER INFORMATION: DNA encoding a codon optimised full-length WT
      MEL TCR alpha chain

<400> SEQUENCE: 31
ctcgagccgc caccatgatg aagagcctgc gggtgctgct ggtgatcctg tggctgcagc      60
tgagctgggt gtggagccag cagaaggagg tggagcagaa cagcggcccc ctgagcgtgc     120
ccgagggcgc catcgccagc ctgaactgca cctacagcga ccggggcagc cagagcttct     180
tctggtatcg gcagtacagc ggcaagagcc ccgagctgat tatgttcatc tacagcaacg     240
gcgacaagga ggacggccgg ttcaccgccc agctgaacaa ggccagccag tatgtgagcc     300
tgctgatccg ggacagccag cccagcgaca gcgccaccta cctgtgcgcc gtgaacgtgg     360
ctgggaagag caccttcggc gacggcacca ccctgaccgt gaagcccaac atccagaacc     420
ccgaccccgc cgtgtaccag ctgcgggaca gcaagagcag cgacaagtct gtgtgcctgt     480
tcaccgactt cgacagccag accaatgtga gccagagcaa ggacagcgac gtgtacatca     540
ccgacaagac cgtgctggac atgcggagca tggacttcaa gagcaacagc gccgtggcct     600
ggagcaacaa gagcgacttc gcctgcgcca acgccttcaa caacagcatc atccccgagg     660 acacctttt t ccccagcccc gagagcagct gcgacgtgaa actggtggag aagagcttcg     720
agaccgacac caacctgaac ttccagaacc tgagcgtgat cggcttcaga atcctgctgc     780
tgaaagtggc tgggttcaac ctgctgatga ccctgcggct gtggagcagc taaacgcgt      839

<210> SEQ ID NO 32
<211> LENGTH: 272
<212> TYPE: PRT
<213> ORGANISM: Homo sapiens

<400> SEQUENCE: 32

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60
```

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Val Ala Gly Lys Ser Thr Phe Gly Asp Gly Thr Thr Leu Thr
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 33
<211> LENGTH: 839
<212> TYPE: DNA
<213> ORGANISM: Artificial Sequence
<220> FEATURE:
<223> OTHER INFORMATION: DNA encoding a high affinity codon optimised
      full-length MEL TCR alpha chain

<400> SEQUENCE: 33
ctcgagccgc caccatgatg aagagcctgc gggtgctgct ggtgatcctg tggctgcagc    60
tgagctgggt gtggagccag cagaaggagg tggagcagaa cagcggcccc ctgagcgtgc   120
ccgagggcgc catcgccagc ctgaactgca cctacagcga ccggggcagc cagagcttct   180
tctggtatcg gcagtacagc ggcaagagcc ccgagctgat tatgttcatc tacagcaacg   240
gcgacaagga ggacggccgg ttcaccgccc agctgaacaa ggccagccag tatgtgagcc   300
tgctgatccg ggacagccag cccagcgaca gcgccaccta cctgtgcgcc gtgaacgacg   360
gcggcagact gaccttcggc gacggcacca ccctgaccgt gaagcccaac atccagaacc   420
ccgaccccgc cgtgtaccag ctgcgggaca gcaagagcag cgacaagtct gtgtgcctgt   480
tcaccgactt cgacagccag accaatgtga gccagcaa ggacagcgac gtgtacatca   540
ccgacaagac cgtgctggac atgcgagca tggacttcaa gagcaacagc gccgtggcct   600
ggagcaacaa gagcgacttc gcctgcgcca acgccttcaa caacagcatc atccccgagg   660 acacctttt ccccagcccc gagagcagct gcgacgtgaa actggtggag aagagcttcg   720
agaccgacac caacctgaac ttccagaacc tgagcgtgat cggcttcaga atcctgctgc   780
tgaaagtggc tgggttcaac ctgctgatga ccctgcggct gtggagcagc taaacgcgt   839

```
<210> SEQ ID NO 34
<211> LENGTH: 272
<212> TYPE: PRT
<213> ORGANISM: Artificial Sequence
<220> FEATURE:
<223> OTHER INFORMATION: A high affinity codon optimised full-length MEL
      TCR alpha chain

<400> SEQUENCE: 34

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Asp Gly Gly Arg Leu Thr Phe Gly Asp Gly Thr Thr Leu Thr
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 35
<211> LENGTH: 839
<212> TYPE: DNA
<213> ORGANISM: Artificial Sequence
<220> FEATURE:
<223> OTHER INFORMATION: DNA encoding a high affinity codon optimised
      full-length MEL TCR alpha chain

<400> SEQUENCE: 35
ctcgagccgc caccatgatg aagagcctgc gggtgctgct ggtgatcctg tggctgcagc      60
tgagctgggt gtggagccag cagaaggagg tggagcagaa cagcggcccc ctgagcgtgc     120
ccgagggcgc catcgccagc ctgaactgca ccctacgcga ccggggcagc cagagcttct     180
tctggtatcg gcagtacagc ggcaagagcc ccgagctgat tatgttcatc tacagcaacg     240
```

-continued

```
gcgacaagga ggacggccgg ttcaccgccc agctgaacaa ggccagccag tatgtgagcc    300
tgctgatccg ggacagccag cccagcgaca gcgccaccta cctgtgcgcc gtgaacgacg    360
gcggcagaag caccttcggc gacggcacca ccctgaccgt gaagcccaac atccagaacc    420
ccgaccccgc cgtgtaccag ctgcgggaca gcaagagcag cgacaagtct gtgtgcctgt    480
tcaccgactt cgacagccag accaatgtga gccagagcaa ggacagcgac gtgtacatca    540
ccgacaagac cgtgctggac atgcgagca tggacttcaa gagcaacagc gccgtggcct    600
ggagcaacaa gagcgacttc gcctgcgcca acgccttcaa caacagcatc atccccgagg    660
acaccttttt ccccagcccc gagagcagct gcgacgtgaa actggtggag aagagcttcg    720
agaccgacac caacctgaac ttccagaacc tgagcgtgat cggcttcaga atcctgctgc    780
tgaaagtggc tgggttcaac ctgctgatga ccctgcggct gtggagcagc taaacgcgt    839
```

<210> SEQ ID NO 36
<211> LENGTH: 272
<212> TYPE: PRT
<213> ORGANISM: Artificial Sequence
<220> FEATURE:
<223> OTHER INFORMATION: A high affinity full-length MEL TCR alpha chain

<400> SEQUENCE: 36

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Asp Gly Gly Arg Ser Thr Phe Gly Asp Gly Thr Thr Leu Thr
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 37
<211> LENGTH: 839
<212> TYPE: DNA
<213> ORGANISM: Artificial Sequence
<220> FEATURE:
<223> OTHER INFORMATION: DNA encoding a high affinity codon optimised
      full-length MEL TCR alpha chain

<400> SEQUENCE: 37

```
ctcgagccgc caccatgatg aagagcctgc gggtgctgct ggtgatcctg tggctgcagc    60
tgagctgggt gtggagccag cagaaggagg tggagcagaa cagcggcccc ctgagcgtgc   120
ccgagggcgc catcgccagc ctgaactgca cctacagcga ccggggcagc cagagcttct   180
tctggtatcg gcagtacagc ggcaagagcc ccgagctgat tatgttcatc tacagcaacg   240
gcgacaagga ggacggccgg ttcaccgccc agctgaacaa ggccagccag tatgtgagcc   300
tgctgatccg ggacagccag cccagcgaca gcgccaccta cctgtgcgcc gtgaacgtgg   360
gcctgatcct gctgttcggc gacggcacca cctgaccgt gaagcccaac atccagaacc   420 ccgacccccgc cgtgtaccag ctgcgggaca gcaagagcag cgacaagtct gtgtgcctgt   480
tcaccgactt cgacagccag accaatgtga gccagagcaa ggacagcgac gtgtacatca   540
ccgacaagac cgtgctggac atgcggagca tggacttcaa gagcaacagc gccgtggcct   600
ggagcaacaa gagcgacttc gcctgcgcca acgccttcaa caacagcatc atccccgagg   660
acaccttttt ccccagcccc gagagcagct gcgacgtgaa actggtggag aagagcttcg   720
agaccgacac caacctgaac ttccagaacc tgagcgtgat cggcttcaga atcctgctgc   780
tgaaagtggc tgggttcaac ctgctgatga ccctgcggct gtggagcagc taaacgcgt    839
```

<210> SEQ ID NO 38
<211> LENGTH: 272
<212> TYPE: PRT
<213> ORGANISM: Artificial Sequence
<220> FEATURE:
<223> OTHER INFORMATION: A high affinity full-length MEL TCR alpha chain

<400> SEQUENCE: 38

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Val Gly Leu Ile Leu Leu Phe Gly Asp Gly Thr Thr Leu Thr
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160
```

```
Ser Gln Thr Asn Val Ser Gln Ser Lys Asp Ser Asp Val Tyr Ile Thr
            165                 170                 175
Asp Lys Thr Val Leu Asp Met Arg Ser Met Asp Phe Lys Ser Asn Ser
        180                 185                 190
Ala Val Ala Trp Ser Asn Lys Ser Asp Phe Ala Cys Ala Asn Ala Phe
    195                 200                 205
Asn Asn Ser Ile Ile Pro Glu Asp Thr Phe Phe Pro Ser Pro Glu Ser
210                 215                 220
Ser Cys Asp Val Lys Leu Val Glu Lys Ser Phe Glu Thr Asp Thr Asn
225                 230                 235                 240
Leu Asn Phe Gln Asn Leu Ser Val Ile Gly Phe Arg Ile Leu Leu Leu
                245                 250                 255
Lys Val Ala Gly Phe Asn Leu Leu Met Thr Leu Arg Leu Trp Ser Ser
            260                 265                 270
```

<210> SEQ ID NO 39
<211> LENGTH: 956
<212> TYPE: DNA
<213> ORGANISM: Artificial Sequence
<220> FEATURE:
<223> OTHER INFORMATION: DNA encoding a codon optimised full-length WT
      MEL TCR beta chain

<400> SEQUENCE: 39

```
ggatccgccg ccaccatgct gtgcagcctg ctggccctgc tgctgggcac cttcttcgga      60
gtgcggagcc agaccatcca ccagtgggcc gccacactgg tgcagcctgt gggcagcccc     120
ctgagcctgg agtgcaccgt ggagggcacc agcaaccccc acctgtactg gtatcggcag     180
gccgcaggga gggggctgca gctgctgttc tactctgtgg catcggcca gatcagcagc      240 gaggtgcccc agaacctgag cgcctccagg ccccaggacc ggcagttcat cctgagcagc     300
aagaagctgc tgctgagcga cagcggcttc tacctgtgcg cctggagcga gaccggcctg     360
ggcaccggcg agctgttctt cggcgagggc tccaggctga ccgtgctgga ggacctgaag     420
aacgtgttcc cccccgaggt ggccgtgttc gagcccagcg aggccgagat cagccacacc     480
cagaaggcta ccctggtgtg tctggccacc ggcttctacc cgaccacgt ggagctgtcc      540 tggtgggtga acggcaagga ggtgcacagc ggcgtgtcta ccgaccccca gcccctgaag     600
gagcagcccg ccctgaacga cagccggtac tgcctgtcct ccagactgag agtgagcgcc     660
accttctggc agaacccccg gaaccacttc cggtgccagg tgcagttcta cggcctgagc     720
gagaacgacg agtggaccca ggaccgggcc aagcccgtga cccagattgt gagcgccgag     780
gcctggggca gagccgactg cggcttcacc agcgagagct accagcaggg cgtgctgagc     840
gccaccatcc tgtacgagat cctgctgggc aaggccaccc tgtacgccgt gctggtgtct     900
gccctggtgc tgatggctat ggtgaagcgg aaggacagcc ggggctaagc ggccgc         956
```

<210> SEQ ID NO 40
<211> LENGTH: 310
<212> TYPE: PRT
<213> ORGANISM: Artificial Sequence
<220> FEATURE:
<223> OTHER INFORMATION: A full-length WT MEL TCR beta chain

<400> SEQUENCE: 40

```
Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30
```

```
Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
 50                      55                  60

Phe Tyr Ser Val Gly Ile Gly Gln Ile Ser Ser Glu Val Pro Gln Asn
 65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Glu
            100                 105                 110

Thr Gly Leu Gly Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 41
<211> LENGTH: 30
<212> TYPE: PRT
<213> ORGANISM: Artificial Sequence
<220> FEATURE:
<223> OTHER INFORMATION: Short scTCR linker

<400> SEQUENCE: 41

Pro Gly Gly Gly Ser Gly Gly Gly Gly Ser Gly Gly Gly Gly Ser Gly
 1               5                  10                  15

Gly Gly Ser Gly Gly Gly Gly Ser Gly Gly Gly Gly Gly Pro
            20                  25                  30

<210> SEQ ID NO 42
<211> LENGTH: 35
<212> TYPE: PRT
<213> ORGANISM: Artificial Sequence
<220> FEATURE:
<223> OTHER INFORMATION: Long scTCR linker

<400> SEQUENCE: 42
```

Pro Gly Gly Gly Ser Gly Gly Gly Ser Gly Gly Gly Ser Gly
1               5                  10                 15

Gly Gly Gly Ser Gly Gly Gly Ser Gly Gly Gly Ser Gly Gly
            20                  25                  30

Gly Gly Pro
        35

<210> SEQ ID NO 43
<211> LENGTH: 9
<212> TYPE: PRT
<213> ORGANISM: Homo sapiens

<400> SEQUENCE: 43

Ala Ala Gly Ile Gly Ile Leu Thr Val
1               5

<210> SEQ ID NO 44
<211> LENGTH: 816
<212> TYPE: DNA
<213> ORGANISM: Homo sapiens

<400> SEQUENCE: 44

| | |
|---|---|
| atgatgaaat ccttgagagt tttactagtg atcctgtggc ttcagttgag ctgggtttgg | 60 |
| agccaacaga aggaggtgga gcagaattct ggacccctca gtgttccaga gggagccatt | 120 |
| gcctctctca actgcactta cagtgaccga ggttcccagt ccttcttctg gtacagacaa | 180 |
| tattctggga aaagccctga gttgataatg ttcatatact ccaatggtga caaagaagat | 240 |
| ggaaggttta cagcacagct caataaagcc agccagtatg tttctctgct catcagagac | 300 |
| tcccagccca gtgattcagc cacctacctc tgtgccgtga cgttgcagg caaatcaacc | 360 |
| tttggggatg ggactacgct cactgtgaag ccaaatatcc agaaccctga ccctgccgtg | 420 |
| taccagctga gagactctaa atccagtgac aagtctgtct gcctattcac cgatttttgat | 480 |
| tctcaaacaa atgtgtcaca agtaaggat tctgatgtgt atatcacaga caaaactgtg | 540 |
| ctagacatga ggtctatgga cttcaagagc aacagtgctg tggcctggag caacaaatct | 600 |
| gactttgcat gtgcaaacgc cttcaacaac agcattattc cagaagacac cttcttcccc | 660 |
| agcccagaaa gttcctgtga tgtcaagctg gtcgagaaaa gctttgaaac agatacgaac | 720 |
| ctaaactttc aaaacctgtc agtgattggg ttccgaatcc tcctcctgaa agtggccggg | 780 |
| tttaatctgc tcatgacgct gcggctgtgg tccagc | 816 |

<210> SEQ ID NO 45
<211> LENGTH: 930
<212> TYPE: DNA
<213> ORGANISM: Homo sapiens

<400> SEQUENCE: 45

| | |
|---|---|
| atgctctgct ctctccttgc ccttctcctg ggcactttct ttggggtcag atctcagact | 60 |
| attcatcaat ggccagcgac cctggtgcag cctgtgggca gcccgctctc tctggagtgc | 120 |
| actgtggagg gaacatcaaa cccccaaccta tactggtacc gacaggctgc aggcaggggc | 180 |
| ctccagctgc tcttctactc cgttggtatt ggccagatca gctctgaggt gccccagaat | 240 |
| ctctcagcct ccagacccca ggaccggcag ttcatcctga gttctaagaa gctcctcctc | 300 |
| agtgactctg gcttctatct ctgtgcctgg tccgagacag ggttaggcac cggggagctg | 360 |
| ttttttggag aaggctctag gctgaccgta ctggaggacc tgaaaaacgt gttcccaccc | 420 |
| gaggtcgctg tgtttgagcc atcagaagca gagatctccc acacccaaaa ggccacactg | 480 |

-continued

```
gtgtgcctgg ccacaggctt ctaccccgac acgtggagc tgagctggtg ggtgaatggg    540
aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc tgtcacccag atcgtcagcg ccgaggcctg ggtagagca     780 gactgtggct tcacctccga gtcttaccag caaggggtcc tgtctgccac catcctctat    840
gagatcttgc tagggaaggc caccttgtat gccgtgctgg tcagtgccct cgtgctgatg    900
gccatggtca agagaaagga ttccagaggc                                     930
```

<210> SEQ ID NO 46
<211> LENGTH: 816
<212> TYPE: DNA
<213> ORGANISM: Artificial Sequence
<220> FEATURE:
<223> OTHER INFORMATION: DNA encoding a high affinity MEL TCR alpha
chain ORF

<400> SEQUENCE: 46

```
atgatgaaat ccttgagagt tttactagtg atcctgtggc ttcagttgag ctgggtttgg     60
agccaacaga aggaggtgga gcagaattct ggaccectca gtgttccaga gggagccatt    120
gcctctctca actgcactta cagtgaccga ggttcccagt ccttcttctg gtacagacaa    180
tattctggga aaagccctga gttgataatg ttcatatact ccaatggtga caaagaagat    240
ggaaggttta cagcacagct caataaagcc agccagtatg tttctctgct catcagagac    300
tcccagccca gtgattcagc acctacctc tgtgccgtga acgatggggg tcgtcttacc    360
tttggggatg gaactacgct cactgtgaag ccaaatatcc agaaccctga ccctgccgtg    420
taccagctga gagactctaa atccagtgac aagtctgtct gcctattcac cgattttgat    480
tctcaaacaa atgtgtcaca aagtaaggat tctgatgtgt atatcacaga caaaactgtg    540
ctagacatga ggtctatgga cttcaagagc aacagtgctg tggcctggag caacaaatct    600
gactttgcat gtgcaaacgc cttcaacaac agcattattc cagaagacac cttcttcccc    660
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagc                              816
```

<210> SEQ ID NO 47
<211> LENGTH: 110
<212> TYPE: PRT
<213> ORGANISM: Artificial Sequence
<220> FEATURE:
<223> OTHER INFORMATION: A high affinity Mel TCR alpha chain variable
domain

<400> SEQUENCE: 47

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Phe Gln Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80
```

```
Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 48

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Phe Leu Gly Ser Gln
                20                  25                  30

Ser Phe Phe Trp Tyr Arg Gln Tyr Ser Gly Lys Ser Pro Glu Leu Ile
            35                  40                  45

Met Phe Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 49
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 49

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Tyr Gln Gly Ala Gln
                20                  25                  30

Ser Phe Phe Trp Tyr Arg Gln Tyr Ser Gly Lys Ser Pro Glu Leu Ile
            35                  40                  45

Met Phe Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 50
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain
```

<400> SEQUENCE: 50

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Ser Ile His Ala Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 51

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asn Leu Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 52
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 52

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Phe Gly Ala Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

```
Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: A high affinity Mel TCR alpha chain variable
      domain

<400> SEQUENCE: 53

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Phe Thr Tyr Arg Glu Gly Asp Lys Glu Asp Gly Arg Phe Thr Ala
    50                  55                  60

Gln Leu Asn Lys Ala Ser Gln His Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro
            100                 105                 110

<210> SEQ ID NO 54
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 54

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Tyr Gly Pro Phe Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu
        115

<210> SEQ ID NO 55
<211> LENGTH: 115
<212> TYPE: PRT
<213> ORGANISM: Artificial Sequence
<220> FEATURE:
```

-continued

<223> OTHER INFORMATION: A high affinity Mel TCR beta chain variable
      domain

<400> SEQUENCE: 55

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Phe Gly Pro Phe Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu
        115

<210> SEQ ID NO 56
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 56

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Phe Gly Pro Tyr Gly Gln Ile Ser Ser Glu Ala Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu
        115

<210> SEQ ID NO 57
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 57

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

```
Asn Leu Tyr Trp Tyr Arg Gln Ala Ala Gly Arg Gly Pro Gln Leu Leu
            35                  40                  45

Phe Tyr Trp Gly Pro Phe Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu
        115

<210> SEQ ID NO 58
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 58

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Met Gly Gly Trp Gln Phe Gly Glu Gly Ser Arg Leu
            100                 105                 110

Thr Val Leu
        115

<210> SEQ ID NO 59
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 59

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80
```

Lys Leu Leu Leu Ser Asp Ser Gly Phe Tyr Leu Cys Ala Trp Ser Glu
                85                  90                  95

Thr Gly Leu Gly Met Gly Gly Trp Ser Phe Gly Glu Gly Ser Arg Leu
            100                 105                 110

Thr Val Leu
        115

<210> SEQ ID NO 60
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 60

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Met Gly Gly Trp Ala Phe Gly Glu Gly Ser Arg Leu
            100                 105                 110

Thr Val Leu
        115

<210> SEQ ID NO 61
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 61

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Val Gly Gly Trp Asp Phe Gly Glu Gly Ser Arg Leu
            100                 105                 110

Thr Val Leu
        115

<210> SEQ ID NO 62
<211> LENGTH: 115
<212> TYPE: PRT
<213> ORGANISM: Artificial Sequence
<220> FEATURE:
<223> OTHER INFORMATION: A high affinity Mel TCR beta chain variable domain

<400> SEQUENCE: 62

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Val Gly Gly Trp Glu Phe Gly Glu Gly Ser Arg Leu
            100                 105                 110

Thr Val Leu
        115
```

<210> SEQ ID NO 63
<211> LENGTH: 115
<212> TYPE: PRT
<213> ORGANISM: Artificial Sequence
<220> FEATURE:
<223> OTHER INFORMATION: A high affinity Mel TCR beta chain variable domain

<400> SEQUENCE: 63

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Val Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Asn Thr Ser Gly Trp Phe Phe Gly Glu Gly Ser Arg Leu
            100                 105                 110

Thr Val Leu
        115
```

<210> SEQ ID NO 64
<211> LENGTH: 115
<212> TYPE: PRT
<213> ORGANISM: Artificial Sequence
<220> FEATURE:
<223> OTHER INFORMATION: A high affinity Mel TCR beta chain variable domain

<400> SEQUENCE: 64

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Asn Thr Asn Gly Trp Phe Phe Gly Glu Gly Ser Arg Leu
            100                 105                 110

Thr Val Leu
        115

<210> SEQ ID NO 65
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 65

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Asn Leu Gly Gly Trp Phe Phe Gly Glu Gly Ser Arg Leu
            100                 105                 110

Thr Val Leu
        115

<210> SEQ ID NO 66
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 66

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
```

```
                    50                  55                  60
Leu Ser Ala Ser Arg Pro Gln Asp Arg Gln Phe Ile Leu Ser Ser Lys
 65                  70                  75                  80

Lys Leu Leu Leu Ser Asp Ser Gly Phe Tyr Leu Cys Ala Trp Ser Glu
                     85                  90                  95

Thr Gly Leu Asn Val Ser Gly Trp Phe Phe Gly Glu Gly Ser Arg Leu
                100                 105                 110

Thr Val Leu
        115

<210> SEQ ID NO 67
<211> LENGTH: 115
<212> TYPE: PRT
<213> ORGANISM: Artificial Sequence
<220> FEATURE:
<223> OTHER INFORMATION: A high affinity Mel TCR beta chain variable
      domain

<400> SEQUENCE: 67

Met Ser Gln Thr Ile His Gln Trp Pro Ala Thr Leu Val Gln Pro Val
 1               5                  10                  15

Gly Ser Pro Leu Ser Leu Glu Cys Thr Val Glu Gly Thr Ser Asn Pro
                 20                  25                  30

Asn Leu Tyr Trp Tyr Arg Gln Ala Ala Gly Arg Gly Leu Gln Leu Leu
             35                  40                  45

Phe Tyr Ser Val Gly Ile Gly Gln Ile Ser Ser Glu Val Pro Gln Asn
 50                  55                  60

Leu Ser Ala Ser Arg Pro Gln Asp Arg Gln Phe Ile Leu Ser Ser Lys
 65                  70                  75                  80

Lys Leu Leu Leu Ser Asp Ser Gly Phe Tyr Leu Cys Ala Trp Ser Glu
                     85                  90                  95

Thr Gly Leu Asn Thr Thr Gly Trp Phe Phe Gly Glu Gly Ser Arg Leu
                100                 105                 110

Thr Val Leu
        115

<210> SEQ ID NO 68
<211> LENGTH: 204
<212> TYPE: PRT
<213> ORGANISM: Artificial Sequence
<220> FEATURE:
<223> OTHER INFORMATION: A soluble high affinity Mel TCR alpha chain
      including an introduced Cys residue

<400> SEQUENCE: 68

Met Gln Lys Glu Val Glu Gln Asn Ser Gly Pro Leu Ser Val Pro Glu
 1               5                  10                  15

Gly Ala Ile Ala Ser Leu Asn Cys Thr Tyr Ser Phe Gln Gly Ser Gln
                 20                  25                  30

Ser Phe Phe Trp Tyr Arg Gln Tyr Ser Gly Lys Ser Pro Glu Leu Ile
             35                  40                  45

Met Phe Ile Tyr Ser Asn Gly Asp Lys Glu Asp Gly Arg Phe Thr Ala
 50                  55                  60

Gln Leu Asn Lys Ala Ser Gln Tyr Val Ser Leu Leu Ile Arg Asp Ser
 65                  70                  75                  80

Gln Pro Ser Asp Ser Ala Thr Tyr Leu Cys Ala Val Asn Val Ala Gly
                 85                  90                  95

Lys Ser Thr Phe Gly Asp Gly Thr Thr Leu Thr Val Lys Pro Asn Ile
                100                 105                 110
```

Gln Asn Pro Asp Pro Ala Val Tyr Gln Leu Arg Asp Ser Lys Ser Ser
            115                 120                 125

Asp Lys Ser Val Cys Leu Phe Thr Asp Phe Asp Ser Gln Thr Asn Val
        130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 69
<211> LENGTH: 204
<212> TYPE: PRT
<213> ORGANISM: Artificial Sequence
<220> FEATURE:
<223> OTHER INFORMATION: A soluble high affinity Mel TCR alpha chain
      including an introduced Cys residue

<400> SEQUENCE: 69

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Phe Leu Gly Ser Gln
            20                  25                  30

Ser Phe Phe Trp Tyr Arg Gln Tyr Ser Gly Lys Ser Pro Glu Leu Ile
        35                  40                  45

Met Phe Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 70
<211> LENGTH: 204
<212> TYPE: PRT
<213> ORGANISM: Artificial Sequence
<220> FEATURE:
<223> OTHER INFORMATION: A soluble high affinity Mel TCR alpha chain
      including an introduced Cys residue

<400> SEQUENCE: 70

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Phe Thr Tyr Arg Glu Gly Asp Lys Glu Asp Gly Arg Phe Thr Ala
        50                  55                  60

Gln Leu Asn Lys Ala Ser Gln His Val Ser Leu Leu Ile Arg Asp Ser
65                  70                  75                  80

Gln Pro Ser Asp Ser Ala Thr Tyr Leu Cys Ala Val Asn Val Ala Gly
                85                  90                  95

Lys Ser Thr Phe Gly Asp Gly Thr Thr Leu Thr Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200
```

<210> SEQ ID NO 71
<211> LENGTH: 245
<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 71

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Pro Gln Leu Leu
            35                  40                  45

Phe Tyr Tyr Gly Pro Phe Gly Gln Ile Ser Ser Glu Val Pro Gln Asn
        50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160
```

```
Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 72
<211> LENGTH: 245
<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 72

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Phe Gly Pro Phe Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 73
<211> LENGTH: 245
```

<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 73

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Phe Gly Pro Tyr Gly Gln Ile Ser Ser Glu Ala Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Thr Gly Glu Leu Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 74
<211> LENGTH: 245
<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 74

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Pro Gln Leu Leu
        35                  40                  45

Phe Tyr Trp Gly Pro Phe Gly Gln Ile Ser Ser Glu Val Pro Gln Asn
    50                  55                  60

Leu Ser Ala Ser Arg Pro Gln Asp Arg Gln Phe Ile Leu Ser Ser Lys

```
                65                  70                  75                  80
Lys Leu Leu Leu Ser Asp Ser Gly Phe Tyr Leu Cys Ala Trp Ser Glu
                    85                  90                  95

Thr Gly Leu Gly Thr Gly Glu Leu Phe Phe Gly Glu Gly Ser Arg Leu
                    100                 105                 110

Thr Val Leu Glu Asp Leu Lys Asn Val Phe Pro Pro Glu Val Ala Val
                    115                 120                 125

Phe Glu Pro Ser Glu Ala Glu Ile Ser His Thr Gln Lys Ala Thr Leu
                    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                    165                 170                 175

Pro Leu Lys Glu Gln Pro Ala Leu Asn Asp Ser Arg Tyr Ala Leu Ser
                    180                 185                 190

Ser Arg Leu Arg Val Ser Ala Thr Phe Trp Gln Asp Pro Arg Asn His
                    195                 200                 205

Phe Arg Cys Gln Val Gln Phe Tyr Gly Leu Ser Glu Asn Asp Glu Trp
                    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 75
<211> LENGTH: 245
<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 75

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                    20                  25                  30

Asn Leu Tyr Trp Tyr Arg Gln Ala Ala Gly Arg Gly Leu Gln Leu Leu
                    35                  40                  45

Phe Tyr Ser Val Gly Ile Gly Gln Ile Ser Ser Glu Val Pro Gln Asn
                    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                    85                  90                  95

Thr Gly Leu Gly Met Gly Gly Trp Gln Phe Gly Glu Gly Ser Arg Leu
                    100                 105                 110

Thr Val Leu Glu Asp Leu Lys Asn Val Phe Pro Pro Glu Val Ala Val
                    115                 120                 125

Phe Glu Pro Ser Glu Ala Glu Ile Ser His Thr Gln Lys Ala Thr Leu
                    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                    165                 170                 175

Pro Leu Lys Glu Gln Pro Ala Leu Asn Asp Ser Arg Tyr Ala Leu Ser
```

-continued

```
                180                 185                 190
Ser Arg Leu Arg Val Ser Ala Thr Phe Trp Gln Asp Pro Arg Asn His
            195                 200                 205

Phe Arg Cys Gln Val Gln Phe Tyr Gly Leu Ser Glu Asn Asp Glu Trp
        210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 76
<211> LENGTH: 245
<212> TYPE: PRT
<213> ORGANISM: Artificial Sequence
<220> FEATURE:
<223> OTHER INFORMATION: A soluble high affinity Mel TCR beta chain
      including an introduced Cys residue

<400> SEQUENCE: 76

Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
            20                  25                  30

Asn Leu Tyr Trp Tyr Arg Gln Ala Ala Gly Arg Gly Leu Gln Leu Leu
        35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Gly Val Gly Gly Trp Glu Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 77
<211> LENGTH: 245
<212> TYPE: PRT
<213> ORGANISM: Artificial Sequence
<220> FEATURE:
<223> OTHER INFORMATION: A soluble high affinity Mel TCR beta chain
``` including an introduced Cys residue

<400> SEQUENCE: 77

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95

Thr Gly Leu Asn Leu Gly Gly Trp Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245
```

<210> SEQ ID NO 78
<211> LENGTH: 245
<212> TYPE: PRT
<213> ORGANISM: Artificial Sequence
<220> FEATURE:
<223> OTHER INFORMATION: A soluble high affinity Mel TCR beta chain including an introduced Cys residue

<400> SEQUENCE: 78

```
Met Ser Gln Thr Ile His Gln Trp Pro Ala Thr Leu Val Gln Pro Val
1               5                   10                  15

Gly Ser Pro Leu Ser Leu Glu Cys Thr Val Glu Gly Thr Ser Asn Pro
                20                  25                  30

Asn Leu Tyr Trp Tyr Arg Gln Ala Ala Gly Arg Gly Leu Gln Leu Leu
            35                  40                  45

Phe Tyr Ser Val Gly Ile Gly Gln Ile Ser Ser Glu Val Pro Gln Asn
    50                  55                  60

Leu Ser Ala Ser Arg Pro Gln Asp Arg Gln Phe Ile Leu Ser Ser Lys
65                  70                  75                  80

Lys Leu Leu Leu Ser Asp Ser Gly Phe Tyr Leu Cys Ala Trp Ser Glu
                85                  90                  95
```

```
Thr Gly Leu Asn Val Ser Gly Trp Phe Phe Gly Glu Gly Ser Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
            245
```